United States Patent
Schnatterer et al.

(10) Patent No.: US 6,670,307 B2
(45) Date of Patent: Dec. 30, 2003

(54) 1,3-OXAZOLINE AND 1,3-THIAZOLINE DERIVATIVES, THEIR PREPARATION, AND THEIR USE AS PESTICIDES

(75) Inventors: Stefan Schnatterer, Hattersheim (DE); Manfred Kern, Lörzweiler (DE); Ulrich Sanft, Eppstein/Ts. (DE); Christina Mertens, Essen (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/886,551

(22) Filed: Jun. 21, 2001

(65) Prior Publication Data

US 2002/0068828 A1 Jun. 6, 2002

Related U.S. Application Data

(62) Division of application No. 09/332,225, filed on Jun. 14, 1999, now Pat. No. 6,265,350.

(30) Foreign Application Priority Data

Jun. 16, 1998 (DE) .......................... 198 26 671

(51) Int. Cl.⁷ .................. C07D 413/14; A01N 43/84
(52) U.S. Cl. .................. 504/225; 504/239; 504/235; 546/269.7; 546/271.4; 546/270.4; 544/124; 544/333; 544/405
(58) Field of Search .................. 504/225, 235, 504/239, 252; 544/124, 333, 405; 546/269.7, 271.4, 270.4

(56) References Cited

U.S. PATENT DOCUMENTS

| | | | |
|---|---|---|---|
| 5,973,162 A | 10/1999 | Alig et al. | 548/203 |
| 6,051,589 A | 4/2000 | Kanellakopulos et al. | 514/374 |
| 6,255,328 B1 | 7/2001 | Alig et al. | 514/365 |

FOREIGN PATENT DOCUMENTS

| | | |
|---|---|---|
| EP | 0345775 | 12/1989 |
| EP | 0432661 | 6/1991 |
| WO | 93/24470 | 12/1993 |
| WO | 95/04726 | 2/1995 |
| WO | 97/06153 | 2/1997 |

OTHER PUBLICATIONS

CA 131:18573, Chelucci et al. 1999.*
CA 103: 53987, Kratrizky et al. (1985).

* cited by examiner

Primary Examiner—Jane Fan
(74) Attorney, Agent, or Firm—Frommer Lawrence & Haug LLP

(57) ABSTRACT

1,3-Oxazoline and 1,3-thiazoline derivatives, their preparation, and their use as pesticides 1,3-Oxazoline and 1,3-thiazoline derivatives of the formula (I)

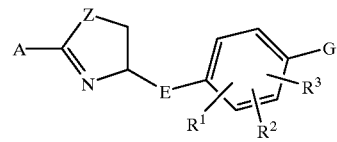

where the symbols have the following meanings:
  A is phenyl, pyridyl, pyrimidinyl, pyrazinyl, pyrazolyl or thienyl,
  E is a single bond, $(C_1-C_4)$alkylene, —O—$CH_2$— or —$CH_2$—O—;
  G is a radical selected from the group consisting of

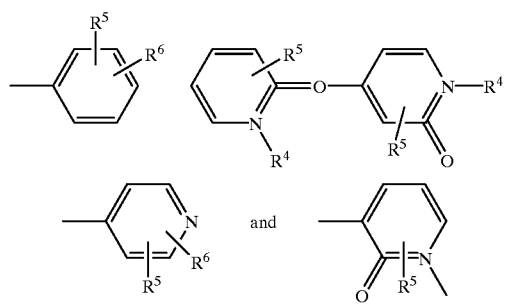

Z is oxygen or sulfur.

Compounds of the formula (I) have, in particular, a very good acaricidal and insecticidal action with regard to the spectrum of action and the potency.

14 Claims, No Drawings

1,3-OXAZOLINE AND 1,3-THIAZOLINE DERIVATIVES, THEIR PREPARATION, AND THEIR USE AS PESTICIDES

This application is a divisional of application U.S. Ser. No. 09/332,225, filed Jun. 14, 1999, now U.S. Pat. No. 6,265,350 and claim priority under 35 U.S.C. §119 to German application 198 26 671, filed Jun. 16, 1998.

DESCRIPTION

The invention relates to diaryl-1,3-oxazolines and -1,3-thiazolines, to processes for their preparation, to compositions comprising them, and to their use for controlling animal pests, in particular insects, spider mites, ectoparasites and helminths.

Because of their biological activity, certain 1,3-oxazolines and 1,3-thiazolines are suitable for controlling animal pests (see, for example, EP-A-0 345 775 and EP-A-0 432 661; WO-A-97/06153; WO-A-93/24470 and WO-A-95/04726).

However, the level of action and/or duration of action of these prior-art compounds is not entirely satisfactory in all fields of application, in particular against certain organisms or when low concentrations are applied.

Since modern pesticides must meet a wide range of demands, for example regarding level, duration and spectrum of action, use spectrum, toxicity, combination with other active substances, combination with formulation auxiliaries or synthesis, and since the occurrence of resistances is possible, the development of such substances can never be regarded as concluded, and there is constantly a high demand for novel compounds which are advantageous over the known compounds, at least as far as some aspects are concerned.

It was an object of the present invention to provide compounds which widen the spectrum of the pesticides in various aspects.

This object, and other objects which are not mentioned explicitly and which can be deduced or concluded from the ideas discussed herein, is solved by 1,3-oxazoline and 1,3-thiazoline derivatives of the formula (I)

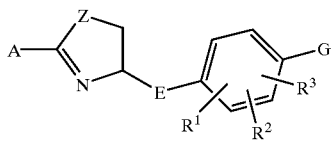

(I)

in which the symbols have the following meanings:
A is phenyl, pyridyl, pyrimidinyl, pyrazinyl, pyrazolyl or thienyl, each of the abovementioned groups optionally being substituted by one or more, preferably one, two or three, radicals X;
X is identical or different
  a) halogen, cyano, nitro;
  b) $(C_1-C_4)$alkyl, $(C_2-C_4)$alkenyl, $(C_2-C_4)$alkynyl, $(C_1-C_4)$alkylthio, $(C_1-C_4)$alkoxy, $(C_1-C_4)$alkylsulfinyl, $(C_3-C_8)$cycloalkyl, $(C_4-C_8)$cycloalkenyl, phenyl, the radicals of group b optionally being substituted by one or more, preferably one, two or three, radicals selected from the group consisting of halogen, cyano, $(C_1-C_4)$alkyl, $(C_1-C_4)$haloalkyl, $(C_1-C_4)$alkoxy and $(C_1-C_4)$haloalkoxy;
E is a single bond, $(C_1-C_4)$alkylene, —O—$CH_2$— or —$CH_2$—O—;

G is a radical selected from the group consisting of:

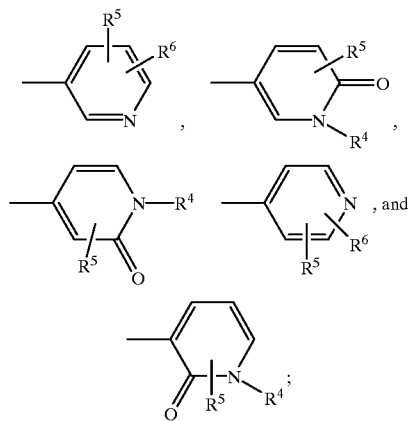

Z is oxygen or sulfur;
$R^1$, $R^2$ and $R^3$ are identical or different hydrogen, halogen, $(C_1-C_4)$haloalkyl, $(C_1-C_4)$alkyl, $(C_1-C_4)$alkoxy, $(C_1-C_4)$haloalkoxy or cyano;
$R^4$ is hydrogen or a group $(C_1-C_8)$alkyl, $(C_2-C_8)$alkenyl, $(C_2-C_8)$alkynyl, $(C_3-C_8)$cycloalkyl, $(C_3-C_8)$cycloalkenyl, $(C_4-C_{10})$cycloalkylalkyl or $(C_7-C_{12})$phenylalkyl, each of the abovementioned groups optionally being substituted by one or more substituents selected from the group consisting of halogen, $(C_1-C_4)$alkyl, $(C_1-C_3)$haloalkyl, $(C_1-C_4)$alkoxy, $(C_1-C_3)$haloalkoxy, $(C_1-C_3)$alkylthio, $(C_3-C_8)$cycloalkyl, $(C_7-C_{12})$phenylalkoxy, $(C_2-C_4)$alkylcarbonyl, alkoxycarbonyl, $(C_2-C_6)$monoalkyl- and $(C_3-C_9)$dialkylamino-carbonyl, cyano and tri$(C_1-C_4)$alkylsilyl;
$R^5$ and $R^6$ are identical or different
  a) hydrogen, halogen, cyano, formyl, $(C_2-C_5)$alkylcarbonyl, $(C_2-C_8)$alkoxycarbonyl, $(C_3-C_9)$monoalkyl- and dialkylamino-carbonyl,
  b) $(C_1-C_8)$alkyl, $(C_3-C_8)$cycloalkyl, $(C_4-C_8)$cycloalkenyl, $(C_1-C_8)$alkoxyalkyl, $(C_1-C_8)$alkylthio, $(C_1-C_8)$alkylsulfinyl, $(C_1-C_8)$alkylsulfonyl, $NR^7R^8$, phenyl, phenoxy, $(C_7-C_{12})$phenylalkyl, $(C_7-C_{12})$phenylalkoxy, heterocyclyl, preferably $(C_4-C_7)$oxacycloalkyl, $(C_4-C_7)$oxacycloalkenyl, $(C_4-C_7)$thiacycloalkyl, $(C_4-C_7)$thiacycloalkenyl, pyridyl, pyrimidinyl, pyrazinyl, furanyl, thienyl, pyrrolyl, imidazolyl, pyrazolyl, triazolyl, thiazolyl, oxadiazolyl, heterocyclyloxy derivatives, hetero-cyclyl$(C_1-C_4)$alkoxy, $(C_3-C_{12})$heterocyclylalkyl, each of the groups b optionally being substituted by one or more, preferably one to three, radicals selected from the group consisting of halogen, $(C_1-C_4)$alkyl, $(C_1-C_3)$haloalkyl, $(C_1-C_3)$alkoxy, $(C_1-C_3)$haloalkoxy, $(C_1-C_3)$alkylthio, $NR^7R^8$, alkylcarbonyl $(C_2-C_5)$, alkoxycarbonyl $(C_2-C_8)$, monoalkyl- and dialkylaminocarbonyl $(C_3-C_9)$, cyano and tri$(C_1-C_4)$alkylsilyl;
  c) $(C_1-C_8)$alkoxy, each of the groups c optionally being substituted by one or more, preferably one to three, radicals selected from the group consisting of halogen, $(C_1-C_3)$alkylthio, $NR^7R^8$, alkylcarbonyl $(C_2-C_5)$, alkoxycarbonyl $(C_2-C_8)$, monoalkyl- and dialkylaminocarbonyl $(C_3-C_9)$, cyano and tri $(C_1-C_4)$alkylsilyl; or
  d) $R^5$ and $R^6$ together form a preferably monocyclic ring which originates by linking two of the groups mentioned under b), preferably $(C_3-C_5)$alkylene, $(C_2-C_4)$alkyleneoxy, $(C_1-C_3)$alkylene-dioxy, $(C_2-C_4)$alkyleneamino or alkylenethio$(C_2-C_4)$;

$R^7$ and $R^8$ are identical or different
  a) hydrogen;
  b) $(C_1-C_8)$alkyl, $(C_3-C_8)$cycloalkyl, $(C_7-C_{12})$phenylalkyl, $(C_1-C_6)$alkyl-carbonyl, $(C_1-C_6)$alkylsulfonyl which are optionally substituted by one or more, preferably one to three, radicals selected from the group consisting of halogen, $(C_1-C_4)$alkyl, $(C_1-C_3)$haloalkyl, $(C_1-C_4)$alkoxy, $(C_1-C_3)$haloalkoxy, $(C_1-C_3)$alkylthio, $(C_1-C_3)$alkyl-amino, $(C_1-C_3)$dialkylamino, $(C_3-C_8)$cycloalkyl, cyano and tri$(C_1-C_4)$alkylsilyl; or
  c) $R^7$ and $R^8$ together are alkylene $(C_3-C_7)$, $(C_3-C_7)$ oxa-, aza- or thiaalkylene, $(C_3-C_7)$alkylenecarbonyl or $(C_3-C_7)$alkylenesulfonyl;

their pure isomers (optical and geometric isomers) and isomer mixtures of these, their N-oxides and their salts which are suitable for use as pesticides.

Surprisingly, compounds of the formula (I) have a better acaricidal and insecticidal activity regarding the spectrum of action and the potency than known 1,3-oxazoline and 1,3-thiazoline derivatives.

The symbols in the formula (I) preferably have the following meanings:

A is preferably phenyl or pyridyl, especially preferably phenyl.

X is preferably
  a) halogen, cyano, nitro or
  b) $(C_1-C_4)$alkyl, $(C_1-C_4)$alkenyl, $(C_1-C_4)$alkynyl, $(C_1-C_4)$alkoxy, $(C_1-C_4)$alkylthio, $(C_1-C_4)$alkylsulfinyl, $(C_3-C_7)$cycloalkyl, $(C_4-C_8)$cycloalkenyl, the radicals of group b optionally being substituted by one or more, preferably one, two or three, radicals selected from the group consisting of halogen, cyano, $(C_1-C_4)$alkoxy and $(C_1-C_4)$haloalkoxy;

X is especially preferably halogen, $(C_1-C_4)$alkyl, $(C_1-C_3)$haloalkyl, $(C_1-C_4)$alkoxy or $(C_1-C_3)$haloalkoxy.

E is preferably a single bond or —CH$_2$—, especially preferably a single bond.

G is preferably

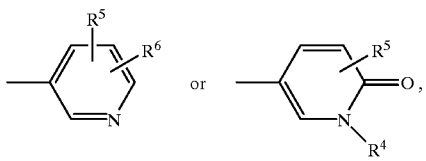

especially preferably 3-pyridyl.

Z is preferably oxygen.

$R^1$, $R^2$, $R^3$ are preferably H, halogen, $(C_1-C_4)$haloalkyl, $(C_1-C_4)$alkyl, $(C_1-C_4)$alkoxy, $(C_1-C_4)$haloalkoxy or cyano, especially preferably H, halogen, $(C_1-C_4)$ haloalkyl, $(C_1-C_4)$alkyl, $(C_1-C_4)$alkoxy, $(C_1-C_4)$ haloalkoxy, $R^4$ is preferably H or $(C_1-C_8)$alkyl which is optionally substituted by one or more, preferably 1 to 3, radicals selected from the group consisting of halogen, $(C_1-C_4)$ alkyl, $(C_1-C_3)$haloalkyl, $(C_1-C_4)$alkoxy, $(C_1-C_3)$ haloalkoxy, $(C_1-C_3)$alkylthio, $(C_3-C_8)$cycloalkyl, cyano or tri$(C_1-C_4)$alkylsilyl.

$R^5$, $R^6$ are preferably
  a) H, halogen, cyano,
  b) $(C_1-C_8)$alkyl, $(C_3-C_8)$cycloalkyl, $(C_4-C_8)$cycloalkenyl, $(C_1-C_8)$alkylthio, $(C_1-C_8)$alkylsulfinyl, $(C_1-C_8)$alkylsulfonyl, $(C_7-C_{12})$phenylalkyl, $(C_7-C_{12})$phenylalkoxy, $(C_4-C_7)$oxycyclo-alkyl or $(C_4-C_7)$oxacycloalkenyl, the groups b optionally being substituted by one or more, preferably 1 to 3, radicals selected from the group consisting of halogen, $(C_1-C_4)$alkyl, $(C_1-C_3)$haloalkyl, $(C_1-C_3)$alkoxy, $(C_1-C_3)$haloalkoxy, $(C_1-C_3)$alkylthio and cyano, c) $(C_1-C_8)$alkoxy which can optionally be substituted by one or more, preferably 1 to 3, radicals selected from the group consisting of halogen, $(C_1-C_3)$ alkylthio and cyano.

$R^5$, $R^6$ are especially preferably
  a) H, halogen, cyano,
  b) $(C_1-C_8)$alkyl, $(C_1-C_8)$alkoxy, $(C_3-C_8)$cycloalkyl, $(C_4-C_8)$cycloalkenyl, $(C_1-C_8)$alkylthio, $(C_1-C_8)$ alkylsulfinyl, $(C_1-C_8)$alkylsulfonyl, $(C_7-C_{12})$ phenylalkyl or $(C_7-C_{12})$phenylalkoxy, the groups b being substituted by one or more, preferably 1 to 3, radicals selected from the group consisting of halogen, $(C_1-C_4)$alkyl, $(C_1-C_3)$haloalkyl and cyano.

In the above formula, "halogen" is to be understood as meaning a fluorine, chlorine, bromine or iodine atom;

the term "$(C_1-C_4)$alkyl" an unbranched or branched hydrocarbon radical having 1 to 4 carbon atoms such as, for example, the methyl, ethyl, propyl, isopropyl, 1-butyl, 2-butyl, 2-methylpropyl or tert-butyl radical;

the term "$(C_1-C_8)$alkyl" the abovementioned alkyl radicals and, for example, the pentyl, 2-methylbutyl, 1,1-dimethylpropyl, hexyl, heptyl, octyl or the 1,1,3,3-tetramethylbutyl radical;

the term "$(C_1-C_4)$haloalkyl" an alkyl group mentioned under the term "$(C_1-C_4)$alkyl" in which one or more hydrogen atoms are replaced by the abovementioned halogen atoms, preferably chlorine or fluorine, such as, for example, the trifluoromethyl group, the 1-fluoroethyl group, the 2,2,2-trifluoroethyl group, the chloromethyl, fluoromethyl group, the difluoromethyl group or the 1,1,2,2-tetrafluoroethyl group;

the term "$(C_3-C_8)$cycloalkyl", for example, the cyclopropyl, cyclobutyl or cyclopentyl group; and the cyclohexyl, cycloheptyl or cyclooctyl radical;

the term "$(C_3-C_8)$halocycloalkyl" one of the abovementioned $(C_3-C_5)$cycloalkyl radicals in which one or more, in the case of fluorine optionally also all, hydrogen atoms are replaced by halogen, preferably fluorine or chlorine, such as, for example, the 2,2-difluoro or 2,2-dichlorocyclopropane group or the fluorocyclopentane radical;

the term "$(C_2-C_4)$alkenyl", for example, the vinyl, allyl, 2-methyl-2-propenyl or 2-butenyl group;

the term "$(C_2-C_4)$haloalkenyl" a $(C_2-C_4)$alkenyl group in which some or, in the case of fluorine also all, of the hydrogen atoms are replaced by halogen, preferably fluorine or chlorine;

the term "$(C_2-C_4)$alkynyl", for example, the ethynyl, propargyl, 2-methyl-2-propynyl or 2-butynyl group;

the term "$(C_2-C_8)$alkynyl" for example, the abovementioned radicals and, for example, the 1-pentynyl, 2-pentynyl, 3-pentynyl, 4-pentynyl or the 1-octynyl group;

the term "$(C_2-C_4)$haloalkynyl" a $(C_2-C_4)$alkynyl group in which some, in the case of fluorine also all, of the hydrogen atoms are replaced by halogen atoms, preferably fluorine or chlorine;

the term "$(C_1–C_4)$hydroxyalkyl", for example, the hydroxymethyl, 1-hydroxyethyl, 2-hydroxyethyl, 1-hydroxy-1-methylethyl or the 1-hydroxypropyl group;

the term "$(C_1–C_4)$alkanoyl-$(C_1–C_4)$alkyl", for example, an acetylmethyl, propionylmethyl, 2-acetylethyl or a butyrylmethyl group;

the term "$(C_1–C_4)$alkanoyl", for example, the formyl, acetyl, propionyl, 2-methylpropionyl or butyryl group;

the term "$(C_1–C_8)$alkanoyl" the abovementioned radicals and, for example, the valeroyl, pivaloyl, hexanoyl, heptanoyl or octanoyl group;

the term "$(C_1–C_2)$alkanoyl", for example, the abovementioned radicals and, for example, the nonanoyl, decanoyl or the dodecanoyl group;

the term "$(C_2–C_4)$haloalkanoyl" a $(C_1–C_4)$alkanoyl group in which some, in the case of fluorine also all, of the hydrogen atoms are replaced by halogen atoms, preferably fluorine or chlorine;

the term "$(C_2–C_{12})$haloalkanoyl" a $(C_1–C_{20})$alkanoyl group in which some, in the case of fluorine also all, of the hydrogen atoms are replaced by halogen atoms, preferably fluorine or chlorine;

the term "cyano$(C_1–C_4)$alkyl" a cyanoalkyl group whose hydrocarbon radical has the meanings given for the term "$(C_1–C_4)$alkyl";

the terms "$(C_1–C_4)$nitroalkyl" or "$(C_1–C_4)$thiocyanoalkyl" one of the abovementioned $(C_1–C_4)$ alkyl groups which are substituted by a nitro or a thiocyano group;

the term "$(C_1–C_4)$alkoxycarbonyl", for example, the methoxycarbonyl, ethoxycarbonyl, propoxycarbonyl, butoxycarbonyl or tert-butoxycarbonyl group;

the term "$(C_1–C_8)$alkoxycarbonyl", for example, the abovementioned radicals and, for example, the pentyloxycarbonyl, hexyloxycarbonyl or the octyloxycarbonyl group;

the term "$(C_1–C_{12})$alkoxycarbonyl" the abovementioned radicals and, for example, the nonyloxycarbonyl, 2-methyloctyloxycarbonyl, decyloxycarbonyl or dodecyloxycarbonyl group;

the term "$(C_1–C_4)$alkoxycarbonyl-$(C_1–C_4)$alkyl", for example, a methoxycarbonylmethyl, ethoxycarbonylmethyl or methoxycarbonylethyl group;

the term "$(C_1–C_4)$haloalkoxycarbonyl" a $(C_1–C_4)$ alkoxycarbonyl group in which one or more, in the case of fluorine optionally also all, hydrogen atoms are replaced by halogen, preferably fluorine or chlorine;

the term "$(C_1–C_4)$alkylthio" an alkylthio group whose hydrocarbon radical has the meaning given for the term "$(C_1–C_4)$alkyl";

the term "$(C_1–C_8)$alkylthio" an alkylthio group whose alkyl radical has the meaning given for the term "$(C_1–C_8)$alkyl";

the term "$(C_1–C_4)$haloalkylthio" a $(C_1–C_4)$alkylthio group in which one or more, in the case of fluorine optionally also all, hydrogen atoms of the hydrocarbon moiety are replaced by halogen, in particular chlorine or fluorine;

the term "$(C_1–C_4)$alkylsulfinyl", for example, the methyl, ethyl, propyl, isopropyl, butyl, isobutyl, sec-butyl- or tert-butylsulfinyl group;

the term "$(C_1–C_8)$alkylsulfinyl" one of the abovementioned alkylsulfinyl groups and, for example, the pentylsulfinyl, 2-methylbutylsulfinyl, hexylsulfinyl or octylsulfinyl group;

the term "$(C_1–C_4)$alkylsulfonyl", for example, the methyl, ethyl, propyl, isopropyl, butyl, isobutyl, sec-butyl or tert-butylsulfonyl group;

the terms "$(C_1–C_4)$haloalkylsulfinyl" and "$(C_1–C_4)$ haloalkylsulfonyl" $(C_1–C_4)$alkylsulfinyl and -sulfonyl radicals having the abovementioned meanings where one or more, in the case of fluorine optionally also all, hydrogen atoms of the hydrocarbon moiety are replaced by halogen, in particular chlorine or fluorine;

the terms "fluoromethylsulfinyl" and "fluoromethylsulfonyl" the mono-, di- and trifluoromethylsulfinyl and -sulfonyl group;

the term "$(C_1–C_4)$alkoxy" an alkoxy group whose hydrocarbon radical has the meaning given for the term "$(C_1–C_4)$alkyl";

the term "$(C_1–C_8)$alkoxy" an alkoxy group whose hydrocarbon radical has the meaning given for the term "$(C_1–C_8)$alkyl";

the term "$(C_1–C_8)$alkylsulfonyl" one of the abovementioned alkylsulfonyl groups and, for example, the pentyl-, 2-methylbutyl-, hexyl-, heptyl- or octylsulfonyl group, the term "$(C_1–C_4)$alkylamino", for example, the methylamino, ethylamino, propylamino, isopropylamino, butylamino, isobutylamino, sec-butylamino or the tert-butylamino group, the term "$(C_1–C_8)$alkylamino" one of the abovementioned $(C_1–C_4)$alkylamino groups and, for example, the pentylamino, hexylamino, heptylamino or octylamino group;

the term "$(C_1–C_4)$dialkylamino", for example, the dimethylamino, methylethylamino, diethylamino, dipropylamino or the dibutylamino group, but also cyclic systems such as, for example, the pyrrolidino or piperidino group, the term "$(C_1–C_8)$dialkylamino" one of the abovementioned $(C_1–C_4)$dialkylamino groups and, for example, the dipentyl, dihexyl or the dioctylamino group;

the term "$(C_1–C_4)$halolkoxy" a haloalkoxy group whose halohydrocarbon radical has the meaning given for the term "$(C_1–C_4)$haloalkyl";

the term "$(C_1–C_4)$alkoxy-$(C_1–C_4)$alkyl", for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the terms "$(C_1–C_4)$haloalkoxy-$(C_1–C_4)$alkyl", "$(C_1–C_4)$ alkoxy-$(C_1–C_4)$haloalkyl" and "$(C_1–C_4)$haloalkoxy-$(C_1–C_4)$haloalkyl" $(C_1–C_4)$alkoxy-$(C_1–C_4)$alkyl radicals having the abovementioned meanings where one or more, in the case of fluorine optionally also all, hydrogen atoms of the relevant hydrocarbon moieties are replaced by halogen, preferably chlorine or fluorine;

the term "$(C_1–C_4)$alkylthio-$(C_1–C_4)$alkyl", for example, methylthiomethyl, ethylthiomethyl, propylthiomethyl, 2-methylthioethyl, 2-ethylthioethyl or 3-methylthiopropyl;

the term "heterocyclyl" a heteroaromatic or heteroaliphatic ring system where "heteroaromatic ring system" is to be understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

the term "heteroaliphatic ring system" a ($C_3$–$C_8$) cycloalkyl radical in which at least one carbon unit is replaced by O, S or a group $NR^{11}$ and $R^{11}$ is hydrogen, ($C_1$–$C_4$)alkyl, ($C_1$–$C_4$)alkoxy or aryl;

the term "heterocyclyloxy" or "heterocyclylthio" one of the abovementioned heterocyclic radicals which are linked via an oxygen or sulfur atom;

the term ($C_3$–$C_8$)cycloalkoxy" or "($C_3$–$C_8$) cycloalkylthio" one of the abovementioned ($C_3$–$C_8$) cycloalkyl radicals which are linked via an oxygen or sulfur atom;

the term "aryl-($C_1$–$C_4$)alkanoyl", for example, the phenylacetyl, 3-phenylpropionyl, 2-phenylpropionyl, 2-methyl-2-phenylpropionyl, 4-phenylbutyryl or the naphthylacetyl group;

the term "($C_3$–$C_8$)cycloalkyl-($C_1$–$C_4$)alkanoyl", for example, the cyclopropylcarbonyl, cyclobutylcarbonyl, cyclopentylcarbonyl, cyclohexylcarbonyl, cyclohexylacetyl or the cyclohexylbutyryl group;

the term "heterocyclyl-($C_1$–$C_4$)alkanoyl", for example, the thenoyl, furoyl, nicotinoyl, thienylacetyl or the pyridinepropionyl group;

the term "($C_3$–$C_8$)cycloalkoxycarbonyl", for example, the cyclobutyloxycarbonyl, cyclopentyloxycarbonyl, cyclohexyloxycarbonyl or the cycloheptyloxycarbonyl group;

the term "($C_3$–$C_8$)cycloalkyl-($C_1$–$C_4$)alkoxycarbonyl", for example, the cyclopropylmethoxycarbonyl, cyclobutylmethoxycarbonyl, cyclopentyloxymethoxycarbonyl, cyclohexyloxymethoxy carbonyl, 1-(cyclohexyl)ethoxycarbonyl or the 2-(cyclohexyl)ethoxycarbonyl group;

the explanation given above applies analogously to homologs or radicals derived therefrom.

The present invention relates to the compounds of the formula (I) in the form of the free base or of an acid addition salt. Acids which can be used for salt formation are inorganic acids such as hydrochloric acid, hydrobromic acid, nitric acid, sulfuric acid, phosphoric acid or organic acids such as formic acid, acetic acid, propionic acid, malonic acid, oxalic acid, fumaric acid, adipic acid, stearic acid, oleic acid, methane sulfonic acid, benzene sulfonic acid or toluene sulfonic acid.

Some of the compounds of the formula (I) have one or more asymmetric carbon atoms or stereoisomers on double bonds. Enantiomers or diastereomers may therefore occur. The invention encompasses not only the pure isomers, but also their mixtures. The diastereomer mixtures can be resolved into the components by customary methods, for example by selective crystallization from suitable solvents or by chromatography. Racemates can be resolved into the enantiomers by customary methods, for example by salt formation with a chiral, enantiomerically pure acid, separation of the diastereomeric salts and liberation of the pure enantiomers by means of a base.

Very especially preferred are the following groups of compounds of the formula (Ia) to (Ie):

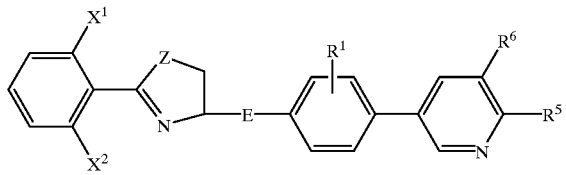

(Ia)

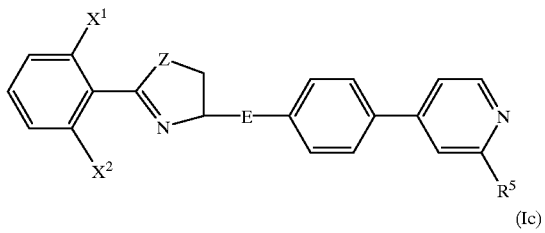

(Ib)

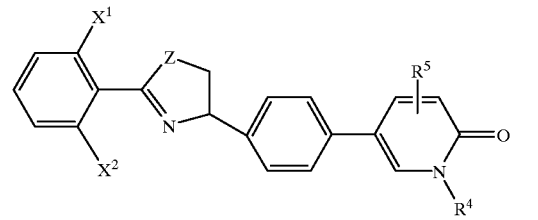

(Ic)

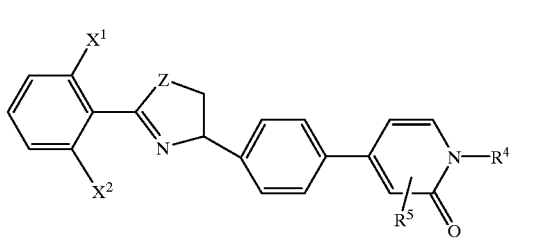

(Id)

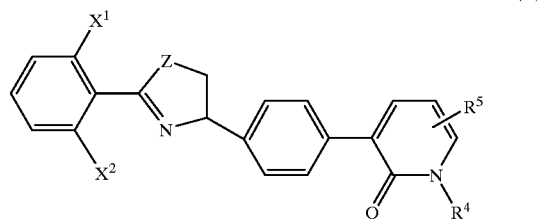

(Ie)

In these formulae $X^1$, $X^2$, Z, $R^4$, $R^5$ and $R^6$ each have the meanings given in the formula (I) ($X^1$, $X^2$=X).

Particularly preferred are compounds of the formula (Ia1) to (Ia4):

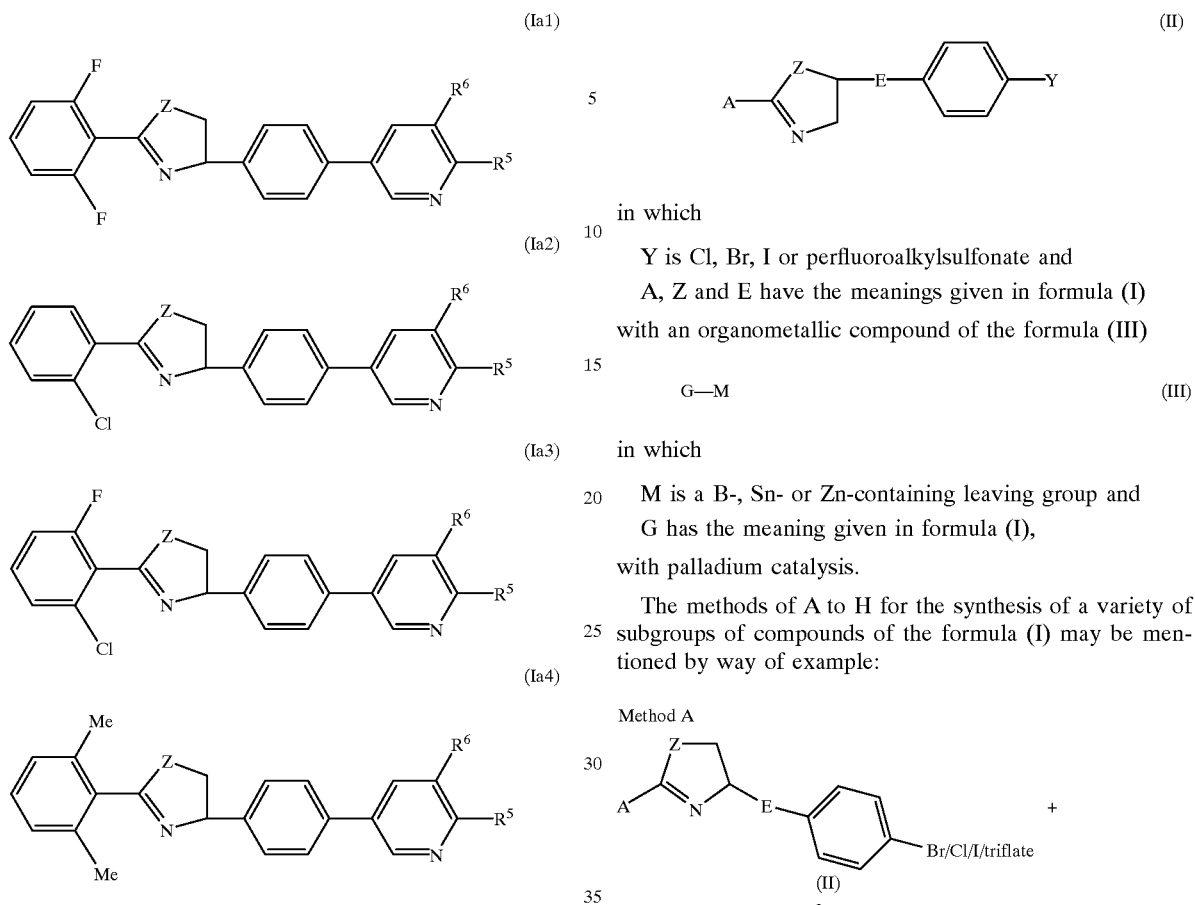

Z, R⁵ and R⁶ each have in this case the meanings given in the formula (I).

The compounds according to the invention are prepared by methods which are known per se from the literature as they are described in standard works on organic synthesis, for example Houben-Weyl, Methoden der Organischen Chemie [Methods in Organic Chemistry], Georg-Thieme-Verlag, Stuttgart.

The preparation is carried out under reaction conditions which are known and suitable for the abovementioned reactions. Other variants which are known per se, but not illustrated here in greater detail, may also be made use of.

If desired, the starting materials may also be formed in situ, in such a way that they are not isolated from the reaction mixture but immediately reacted further to give the compounds of the formula (I).

The general chemistry of the 1,3-oxazolines is described, for example, in Tetrahedron, 1994, 50, 2297–2360 and in Nachr. Chem. Tech. Lab. 1996, 44, 744–750.

The invention also relates to a process for the preparation of compounds of the formula (I) by reacting known 1,3-oxazolines and 1,3-thiazolines of the formula (II) (see, for example, EP-A-0 345 775) (suitably substituted by R¹, R², R³) with metalloid-pyridine compounds of the formula (III) (suitably substituted by R⁴, R⁵, R⁶), which comprises reacting a halogen and perfluoroalkylsulfonate compound of the formula (II)

in which

Y is Cl, Br, I or perfluoroalkylsulfonate and

A, Z and E have the meanings given in formula (I)

with an organometallic compound of the formula (III)

G—M       (III)

in which

M is a B-, Sn- or Zn-containing leaving group and

G has the meaning given in formula (I), with palladium catalysis.

The methods of A to H for the synthesis of a variety of subgroups of compounds of the formula (I) may be mentioned by way of example:

Method A

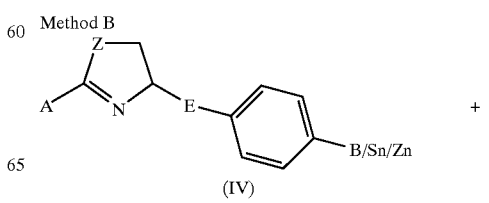

G = 3-pyridyl, 4-pyridyl, 2-pyridon-5-yl, 2-pyridon-3-yl (cf. formula (I)).

Linkage of the phenyl ring with a pyridine ring is effected, for example, by palladium catalysis using Suzuki coupling, Stille coupling or Negishi coupling (see, for example, P. Knochel, Chem. Review 1993, 93, 2117–2188 or Jiro Tsuji, Palladium Reagents and Catalysts, John Wiley & Sons, 1996).

It is also possible for the functions required for the linkage to be swapped between (II) and (III):

Method B

-continued

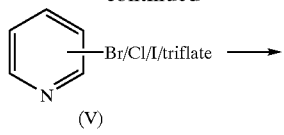

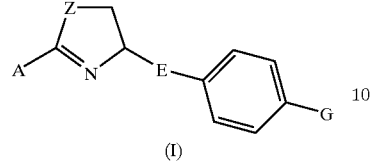

It is also possible first to construct a pyridyl-phenyl structural unit and to convert these precursors into 1,3-oxazolines and 1,3-thiazolines of the formula (I).

Method C

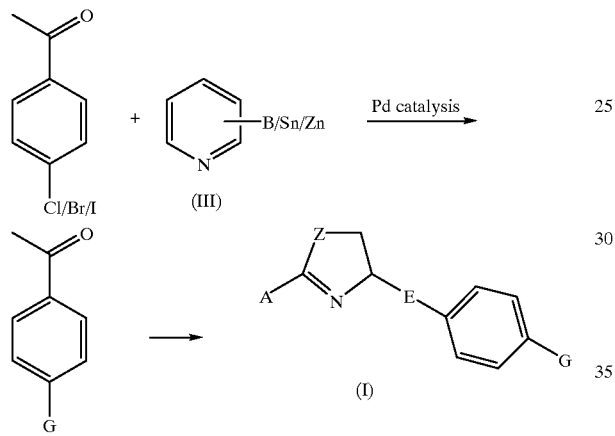

The oxazoline precursors of the formula (II) are prepared, for example, by the following routes, some of which are known (EP-A-0 432 661; G. Helmchen, Tetrahedron 1996, 52, 7547–7583)):

Activated carboxylic acid derivatives are reacted with aminoalcohols (VI) (suitably substituted by $R^1$, $R^2$, $R^3$) (Synthesis K. Drauz, J. Org. Chem. 1993, 58, 3568–3571) to give the amidoalcohols (VII):

Method D (Ex. VP3)

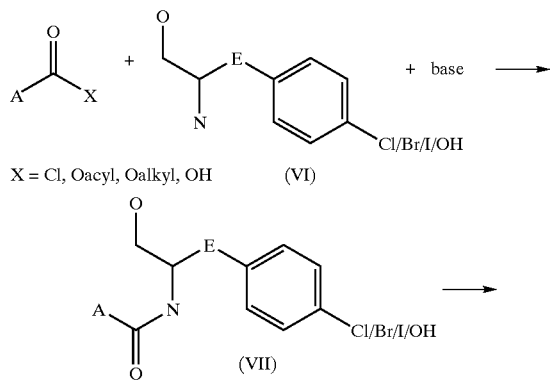

-continued

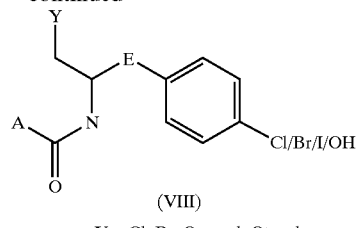

Y = Cl, Br, Omesyl, Otosyl

The chlorides (VIII) (Y=Cl) are obtained from the amidoalcohols (VII) for example using thionyl chloride; when sulfone halides are used, the sulfonates (VII) (Y=for example mesylate, tosylate) are formed.

The oxazolines (II) are formed from (VIII) by the action of bases.

Method E (Ex. VP4)

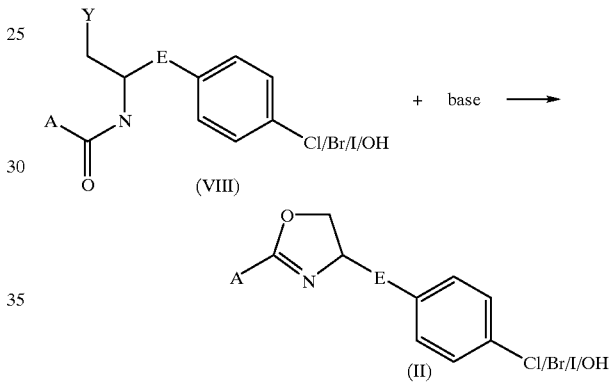

Y = Cl, Br, Omesyl, Otosyl

Bases which are suitable are, for example, basic salts such as alkali metal hydroxides, alkali metal carbonates, hydrides, alkoxides and amines. Starting from the 4-hydroxyphenyl derivatives of (II), the triflates may be obtained by sulfonation with, for example, trifluoromethanesulfonyl chloride.

The oxazoline precursors of the formula (IV) which contain a tin group are accessible by Stille coupling with distannane:

Method F (Ex. VP5)

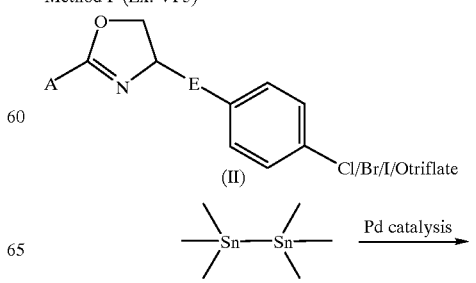

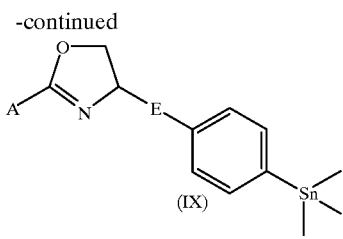

The pyridine precursors of the formula (III) are formed, for example, by generating metalated pyridine derivatives with the suitable substituents $R^4$, $R^5$, $R^6$ as per formula (I) and their reaction with, for example, boric esters, tin halides or zinc halides.

Method G  (Ex. VP7, VP8)

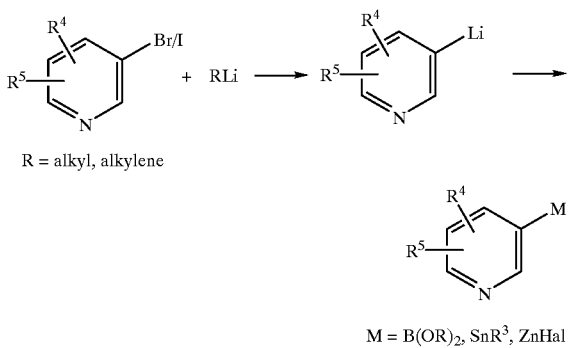

The aminoalcohol precursors (VI) can be prepared by reducing known 2-hydroxyacetophenone oximes by means of hydride.

Method H  (Ex. VP2)

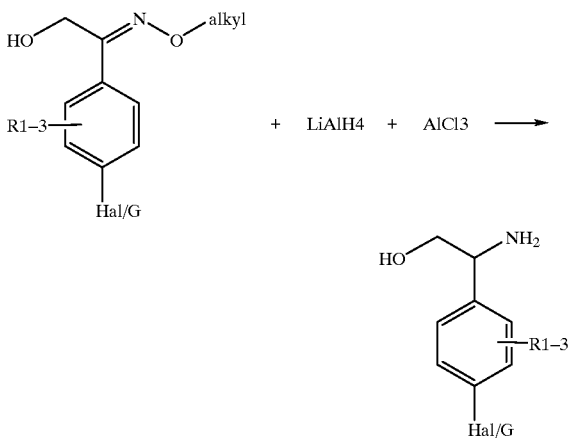

Collections of compounds of the formula (I) which can be synthesized by the abovementioned scheme may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as it is described, for example, by S. H. DeWitt in "Annual Reports in Combinatorial Chemistry and Molecular Diversity: Automated synthesis", Volume 1, Verlag Escom 1997, pages 69 to 77.

A series of commercially available apparatuses as they are offered by, for example, Stem Corporation, Woodrolfe Road, Tollesbury, Essex, CM9 8SE, England or H+P Labortechnik GmbH, Bruckmannring 28, 85764 Oberschleißheim, Germany, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin.

Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries. The present invention also relates to libraries which comprise at least two compounds of the formula (I).

The compounds of the formula (I) are suitable for controlling animal pests, in particular insects, arachnids, helminths and mollusks, very especially preferably for controlling insects and arachnids which are encountered in agriculture, in livestock breeding, in forests, in the protection of stored goods and materials, and in the hygiene sector, and have good plant tolerance and favorable toxicity to warm-blooded species. They are active against normally sensitive and resistant species and against all or individual developmental stages. The abovementioned pests include:

from the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp., Eutetranychus spp.

From the order of the Isopoda, for example, *Oniscus aselus, Armadium vulgare, Porcellio scaber.*

From the order of the Diplopoda, for example, *Blaniulus guttulatus.*

From the order of the Chilopoda, for example, *Geophilus carpophagus*, Scutigera spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis, Schistocerca gregaria*.

From the order of the Isoptera, for example, Reticulitermes spp.

From the order of the Anoplura, for example, *Phylloera vastatrix*, Pemphigus spp., *Pediculus humanus corporis*, Haematopinus spp., Linognathus spp.

From the order of the Mallophaga, for example, Trichodectes pp., Damalinea spp.

From the order of the Thysanoptera, for example, *Hercinothrips femoralis, Thrips tabaci*.

From the order of the Heteroptera, for example, Eurygaster spp., *Dysdercus intermedius, Piesma quadrata, Cimex lectularius, Rhodnius prolixus*, Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon soistitialis, Costelytra zealandica*.

From the order of the Hymenoptera, for example, Diprion spp., Hoplocampa spp., Lasius spp., *Monomorium pharaonis*, Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*.

From the order of the Siphonaptera, for example, *Xenopsylla cheopsis*, Ceratophyllus spp.

From the order of the Arachnida, for example, *Scorpio maurus, Latrodectus mactans*.

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the Gastropoda, for example, Deroceras spp., Arion spp., Lymnaea spp., Galba spp., Succinea spp., Biomphalaria spp., Bulinus spp., Oncomelania spp.

From the class of the Bivalva, for example, Dreissena spp.

The plant-parasitic nematodes which can be controlled in accordance with the invention include, for example, the root-parasitic soil-dwelling nematodes such as, for example, those of the genera Meloidogyne (root knot nematodes, such as *Meloidogyne incognita, Meloidogyne hapla* and *Meloidogyne javanica*), Heterodera and Globodera (cyst-forming nematodes, such as *Globodera rostochiensis, Globodera pallida, Heterodera trifolii*) and of the genera Radopholus, such as *Radopholus similis*, Pratylenchus such as *Pratylenchus neglectus, Pratylenchus penetrans* and *Pratylenchus curvitatus*; Tylenchulus such as *Tylenchulus semipenetrans*, Tylenchorhynchus, such as *Tylenchorhynchus dubius* and *Tylenchorhynchus daytoni*, Rotylenchus such as *Rotylenchus robustus*, Heliocotylenchus such as *Haliocotylenchus multicinctus*, Belonoaimus such as *Belonoaimus longicaudatus*, Longidorus such as *Longidorus elongatus*, Trichodorus such *Trichodorus primitivus* and Xiphinema such as *Xiphinema index*.

Other nematode genera which can be controlled using the compounds according to the invention are Ditylenchus (stem parasites, such as *Ditylenchus dipsaci* and *Ditylenchus destructor*), Aphelenchoides (foliar nematodes, such as *Aphelenchoides ritzemabosi*) and Anguina (seed nematodes, such as *Anguina tritici*).

The invention also relates to compositions, for example crop protection compositions, preferably insecticidal, acaricidal, ixodicidal, nematicidal, molluskicidal or fungicidal, especially preferably insecticidal and acaricidal, compositions which comprise one or more compounds of the formula (I) in addition to suitable formulation auxiliaries.

In general, the compositions according to the invention comprise 1 to 95% by weight of the active substances of the formula (I).

To prepare the compositions according to the invention, the active substance and the other additives are combined and brought into suitable use form.

They can be formulated in various ways, depending on the biological and/or chemical-physical parameters which prevail. The following are examples of possible formulations:

Wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and absorption granules, water-dispersible granules (WG), ULV formulations, microcapsules, waxes or baits.

These individual types of formulations are known in principle and are described, for example, in:

Winnacker-Küchler, "Chemical Technology", Volume 7, C. Hauser Veriag Munich, 4th Edition 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxilairies such as inert materials, surfactants, solvents and other additives, are also known and described, for example, in Watkins, "Handbook of Insecticide Dust Diluents and Garriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active ethylene oxide adducts] Wiss. Verlagsgesell., Stuttgart 1967; Winnacker-Küchler, "Chemische Technologie", Volume 7, C. Hauser Verlag Munich, 4th Edition 1986.

Based on these formulations, it is also possible to prepare combinations with other pesticidally active materials, fertilizers and/or growth regulators, for example in the form of a ready-mix formulation or a tank mix. Wettable powders are preparations which are uniformly dispersible in water which, besides the active substance, also comprise wetters, for example polyoxyethylated alkylphenols, polyoxyethylated fatty alcohols, alkylsulfonates or alkylphenolsulfonates and dispersants, for example sodium lignosulfonate or sodium 2,2'-dinaphthylmethane-6,6'-disulfonate, in addition to a diluent or inert material.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. As emulsifiers, the following can be used, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained, for example, by grinding the active substance with finely divided solid materials, for example talc or natural clays, such as kaolin, bentonite, pyrophyllite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or else mineral oils. Suitable active substances can also be granulated in the manner which is customary for the preparation of fertilizer granules, if desired as a mixture with fertilizers.

The active substance concentration in wettable powders is, for example, approximately 10 to 90% by weight, the remainder to 100% by weight is composed of customary formulation auxiliaries. In the case of emulsifiable concentrates, the active substance concentration may be approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

Besides, the abovementioned active substance formulations comprise, if appropriate, the tackifiers, wetters, dispersants, emulsifiers, penetrants, solvents, fillers or carriers which are conventional in each case.

For use, the concentrates, which are present in commercially available form, are, if desired, diluted in the customary manner, for example in the case of wettable powders, emulsifiable concentrates, dispersions and in some cases also microgranules using water. Preparations in the form of dusts and granules and sprayable solutions are usually not diluted any further with other inert substances prior to use.

The application rate required varies with the external conditions such as, inter alia, temperature and humidity. It may vary within wide limits, for example between 0.0005 and 10.0 kg/ha or more of active substance, but it is preferably between 0.001 and 5 kg/ha.

The active substances according to the invention, in their commercially available formulations and in the use forms prepared from these formulations (see the abovementioned compositions) may be present in mixtures with other active substances such as insecticides, attractants, sterilants, acaricides, nematicides, fungicides, molluskicides, growth regulatory substances or herbicides.

The pesticides include, for example, phosphoric esters, carbamates, carboxylic esters, formamidines, tin compounds and materials produced by microorganisms.

Preferred components in mixtures are:

1. from the group of the phosphorus compounds acephate, azamethiphos, azinphos-ethyl, azinphos-methyl, bromophos, bromophos-ethyl, cadusafos (F67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;

2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl)carbamate, oxamyl, pirimicarb, propoxur, thiodicarb, thiofanox, 1-methylthio(ethylideneamino)-N-methyl-N-(morpholinothio)carbamate (UC 51717), triazamate;

3. from the group of the carboxylic esters acrinathrin, allethrin, alphametrin, 5-benzyl-3-furylmethyl (E)-(1R)-cis-2,2-dimethyl-3-(2-oxothiolan-3-ylidenemethyl)cyclopropanecarboxylate, beta-Cyfluthrin, beta-cypermethrin, bioallethrin, bioallethrin ((S)-cyclopentylisomer), bioresmethrin, bifenthrin, (RS)-1-cyano-1-(6-phenoxy-2-pyridyl)methyl(1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-1311), lambda-cyhalothrin, permethrin, phenothrin ((R) isomer), prallethrin, pyrethrins (natural products), resmethrin, tefluthrin, tetramethrin, theta-Cypermethrin (TD-2344), tralomethrin, transfluthrin, zeta-cypermethrin (F-56701);

4. from the group of the amidines amitraz, chlordimeform;

5. from the group of the tin compounds cyhexatin, fenbutatin oxide;

6. others abamectin, ABG-9008, acetamiprid, anagrapha falcitera, AKD-1022, AKD-3059, ANS-118, *bacillus thuringiensis, beauveria bassianea*, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropanecarboxylate (Ro12-0470), cyromazin, diacloden (thiamethoxam), diafenthiuron, ethyl 2-chloro-N-(3,5-dichloro-4-(1,1,2,3,3,3-hexafluoro-1-propyloxy)phenyl)carbamoyl)-2-carboximidate, DDT, dicofol, diflubenzuron, N-(2,3-dihydro-3-methyl-1,3-thiazol-2-ylidene)-2,4-xylidine, dinobuton, dinocap, diofenolan, DPX-062, emamectin benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE_473), hexythiazox, HOI-9004, hydramethyinon (AC 217300), lufenuron, imidacloprid, indoxacarb (DPX-MP062), kanemite (AKD-2023), M-020, MTI-446, ivermectin, M-020, methoxyfenozide (intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), Pyriproxyfen (S-71639), NC-196, NC-1111, NNI-9768, Novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (mykotal), YI-5301.

The active substance content of the use forms prepared from the commercially available formulations may range from 0.00000001 up to 95% by weight of active substance, preferably between 0.00001 and 1% by weight. Application is effected in a customary manner adapted to suit the use forms.

The invention also relates to a method of controlling harmful insects, Acarina, mollusks and/or nematodes in which an effective amount of a compound according to the invention or of a composition according to the invention is applied to these or to the plants, areas or substrates infested with them.

The use of a compound according to the invention or of a composition according to the invention for controlling harmful insects, Acarina, mollusks and/or nematodes is also the subject of the invention.

The active substances according to the invention are also suitable for use in the veterinary medicine sector, preferably for controlling endoparasites and ectoparasites, and in the field of animal keeping.

The active substances according to the invention may be applied in the known manner, such as by oral administration in the form of, for example, tablets, capsules, drinks or granules, by dermal application in the form of, for example, dipping, spraying, pouring on and spotting on, and dusting, and by parenteral administration in the form of, for example, an injection.

In addition, the compounds according to the invention are also suitable for use in technology, for example as wood preservative, as preservative in paints, in cooling lubricants for metalworking, or as preservative in drilling and cutting oils.

Accordingly, the compounds of the formula (I) according to the invention can also be employed particularly advantageously in livestock keeping (for example cattle, sheep, pigs and poultry such as chickens, geese and the like). In a preferred embodiment of the invention, the novel compounds, if appropriate in suitable formulations (cf. above), are administered orally to the animals, if appropriate together with the drinking water or feed. Since excretion in the feces is highly efficient, the development of insects in the animals' feces can be prevented very easily in this manner. The dosages and formulations which are suitable in each case depend, in particular, on the species and the developmental stage of the productive livestock and also on the risk of infestation and can be determined readily and established by customary methods. For example, the compounds can be employed in cattle at dosages of 0.01 to 1 mg/kg body-weight.

The compounds of the formula (I) according to the invention are also distinguished by an outstanding fungicidal action. Fungal pathogens which have already penetrated the plant tissue can be controlled successfully in a curative manner. This is especially important and advantageous in the case of those fungal diseases which can no longer be controlled effectively by the fungicides which are otherwise customary once infection has taken place. The spectrum of action of the claimed compounds encompasses a variety of economically important phytopathogenic fungi such as, for example, *Plasmopara viticola, Phytophthora infestans, Erysiphe graminis, Pyricularia oryzae, Pyrenophora teres, Leptosphaerea nodorum* and *Pellicularia sasakii* and *Puccinia recondite.*

These, but also predominantly insecticidally, acaricidally, molluskicidally or nematocidally active compounds of the formula (I), can be applied, in their commercially available formulations, either alone or in combination with other fungicides known from the literature.

Fungicides which are known from the literature and which can be combined in accordance with the invention with the compounds of the formula (I) are, for example, the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezine, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazol, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconaxole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, dioctylsodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quarternized fatty amines, alkyldimethylbenzylammonium chloride and 1-hydroxyethyl-2-alkyl-imidazoline.

The abovementioned components for combinations are known active substances, many of which are described in C. D. S. Tomlin, S. B. Walker, The Pesticide Manual, 11th Edition, British Crop Protection Council, Farnham 1997.

The active substance content of the use forms prepared from the commercially available formulations can be varied within wide ranges, the active substance concentration of the use forms may range from 0.0001 up to 95% by weight of active substance, preferably from 0.0001 to 1% by weight. They are applied in a customary manner adapted to suit the use forms.

They are used in a customary manner adapted to suit the use forms, for example by applying, in order to control pathogenic fungi, a fungicidally effective amount of a compound according to the invention or of a composition according to the invention to these fungi or to the plants, areas of substrates infested with them, or to seed.

The invention also relates to seed, treated or coated with an effective amount of a compound according to the invention or of a composition according to the invention.

The compounds of the formula (I) can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formula (I) for controlling harmful organisms in transgenic crop plants.

The use according to the invention of compounds of the formula (I) or of compositions comprising them, for example as insecticide, acaricide, molluskicide, nematicide or fungicide, also includes the case where the compound of the formula (I) or its salt is formed from a precursor only after application, for example in the insect, in a plant or in the soil.

The contents of the German Patent Application 198 15 026.1, whose priority is claimed by the present application, and the contents of the appended summary are therefore expressly incorporated by reference; they are part of the present description by way of quotation.

The examples which follow are intended to illustrate the invention without restricting it thereto.

A. PREPARATION EXAMPLES

Precursor VP 1: 4'-bromo-2-hydroxyacetophenone O-methyloxime

Sodium formate (244.6 g, 3597 mmol) was introduced into ethanol/water 7:3 (1 l). 2,4'-dibromoacetophenone (200 g, 719 mmol) was added portionwise at approx. 60° C., and the mixture was then refluxed for 7 hours. Water (1 l) was then admixed. Upon cooling, the hydroxy ketone crystallized and was isolated by filtration with suction. This gave the hydroxy ketone intermediate (143.6 g,=93% yield) in its pure form. It was mixed with O-methylhydroxylamine hydrochloride (59.0 g, 706 mmol) and sodium acetate (57.9 g, 706 mmol) in dioxane/water 9:1 (700 ml) and the mixture was refluxed for 3 hours. After stirring with water (1.3 l) and extraction with heptane/ethyl acetate 1:1, 4'-bromo-2-hydroxy-acetophenone O-methyloxime, 174.3 g, was obtained as an oil, purity approx. 90%, 2 isomers.

Precursor VP2: 2-amino-2-(4-bromophenyl)ethanol (Amino Alcohol of the Formula VI)

4'-bromo-2-hydroxyacetophenone O-methyloxime (54.8 g, 224 mmol) were added dropwise at 20° C. under nitrogen as a solution in THF to a mixture of lithium aluminum hydride (20 g, 505 mmol) and aluminum chloride (15.3 g, 112 mmol) in THF (350 ml). After 4 hours, the mixture was hydrolyzed (40 ml methanol; 200 ml 2N NaOH) and extracted with heptane/ethyl acetate. The crude product (42 g) was recrystallized from heptane/ethyl acetate 2:1. This gave 2-amino-2-(4-bromophenyl)ethanol, 29.3 g, colorless crystals, m.p. 95° C.

Precursor VP3: N-[1-(4'-bromophenyl)-2-hydroxyethyl]-2,6-difluorobenzamide (Formula VII)

2,6-difluorobenzoyl chloride (13.8 ml, 110 mmol) was added dropwise at 20° C. to 2-amino-2-(4-bromophenyl)

ethanol (25.0 g, 116 mmol) and triethylamine (19.5 ml, 139 mmol) in THF (150 ml). After 15 hours, the mixture was stirred with water and extracted with heptane/ethyl acetate. This gave the amido alcohol product, 38.6 g, pale yellow solid, m.p. 141° C.

Precursor VP4: 2-(2,6-difluorophenyl)-4-(4-bromophenyl)oxazoline (Formula II)

Synthesis Using the Thionyl Chloride/Alkali Metal Hydroxide Method

The amido alcohol VP3 (38.5 g, 108 mmol) was mixed in dichloromethane with thionyl chloride (9.7 ml, 130 mmol) and heated for 5 hours at 40° C. The mixture was concentrated and the residue (=amidochloride, 36.5 g) was refluxed with 6N NaOH (32.5 ml) in dioxane (180 ml) (6 hours). The mixture was stirred with water and extracted with ethyl acetate. The crude product (oil, 31.8 g) was recrystallized from heptane/ethyl acetate 9:1. This gave 2-(2,6-difluorophenyl)-4-(4-bromophenyl)oxazoline, 17.8 g, colorless crystals, m.p. 98° C.; b.p. 365° C. (GC).

Synthesis Using the Tosyl Chloride/Amine Method

The amido alcohol VP3 (5.0 g, 14.0 mmol) was mixed in dichloromethane (40 ml) with triethylamine (5.67 g, 56 mmol) and tosyl chloride (2.94 g, 15.5 mmol) and refluxed for 5 hours. The mixture was concentrated, and the residue was stirred with water and extracted with ethyl acetate. The crude product (4.6 g) was recrystallized with ethanol/water 8:2. This gave 2-(2,6-difluorophenyl)-4-(4-bromophenyl)oxazoline, 3.4 g, colorless crystals, m.p. 97° C.; $^1$H NMR (CDCl$_3$, ppm): 4.24, 4.81, 5.43, oxazoline; 7.00, 7.43, F2C6H3; 7.23, 7.51, BrC$_6$H$_4$.

Precursor VP5: 2-(2,6-difluorophenyl)-4-(4-trimethylstannylphenyl)oxazoline (Formula IX)

VP3 2-(2,6-difluorophenyl)-4-(4-bromophenyl)oxazoline (16.4 g, 48.8 mmol) was introduced into dioxane under nitrogen, hexamethyldistannane (20 g, 61.2 mmol), Pd(PPh$_3$)$_4$ (1.4 g, 1.2 mmol) and lithium chloride (0.38 g, 4.4 mmol) were added and the mixture was refluxed for 7 hours. The reaction mixture was stirred with water and extracted with heptane/ethyl acetate. The crude product (19.6 g, oil) contained approximately 70% of the Sn product. Separation by chromatography (eluent: heptane/ethyl acetate 2:1) yielded 2-(2,6-difluorophenyl)-4-(4-trimethylstannylphenyl)oxazoline, 13.4 g, oil, turned crystalline, DC Rf 0.59 (VP4 Rf 0.49).

Precursor VP6: 5-bromo-2-trifluorethoxypyridine

Sodium hydride (18.6 g, 60%, 464 mmol) was introduced into DMF (500 ml) under nitrogen. Trifluoroethanol (32.2 ml, 443 mmol) was added dropwise at 10° C. After 1 hour, 2,5-dibromopyridine (100 g, 422 mmol) was added portionwise, and the mixture was stirred in a water bath for 24 hours at 20° C. It was then stirred with water and extracted with heptane/ethyl acetate 9:1. Distillation of the crude product (105 g) yielded 5-bromo-2-trifluoroethoxypyridine, 82.1 g (purity 93%), colorless fluid, b.p. 97–104° C. at 18 mbar.

Other alkoxypyridines and alkylthiopyridines were prepared analogously.

Precursor VP7: 5,5-dimethyl-2-(2-trifluoroethoxypyridin-5-yl)-1,3,2-dioxaborinane 5-Bromo-2-trifluoroethoxypyridine (30.0 g, 117 mmol) was introduced into THF/diethyl ether 2:1 (250 ml) under nitrogen and cooled. An n-butyllithium solution (2.5 M, 53.9 ml, 135 mmol) was added at approx. −85° C. using a syringe. After 10 minutes, isopropyl borate (33.1 ml, 141 mmol) was added dropwise at approx. −80° C. The temperature of the mixture was allowed to climb to −10° C., and acetic acid (10.1 ml, 176 mmol) and 2,2-dimethylpropanediol (15.9 g, 152 mmol) were added. After 15 hours at 20° C., the mixture was stirred with water and extracted with heptane/ethyl acetate. The crude product (31.5 g) was recrystallized using heptane/ethyl acetate 95:5. This gave 5,5-dimethyl-2-(2-trifluoroethoxypyridin-5-yl)-1,3,2-dioxaborinane, 20.3 g, white solid; $^1$H NMR (CDCl$_3$, ppm): 1.02, Me; 3.75, OCH$_2$; 4.77, PyOCH$_2$; 6.82, 7.97, 8.50, PyH.

Other 2-pyridyl-1,3,2-dioxaborinanes were prepared analogously.

Precursor VP8: 2-Ethoxy-5-trimethylstannylpyridine

5-Bromo-2-ethoxypyridine (14.9 g, 68 mmol) were introduced into THF/diethyl ether 2:1 (120 ml) under nitrogen. n-Butyllithium/hexane solution (2.5 M, 33 ml, 82 mmol) was added at −80° C. After 15 minutes, chlorotrimethyltin (16.4 g, 82 mmol), dissolved in THF, was added dropwise. The temperature of the mixture was allowed to rise to 0° C., and the mixture was stirred with water and extracted with heptane/ethyl acetate. The crude product (15.7 g) was distilled in vacuo. This gave 2-ethoxy-5-trimethylstannylpyridine, 11.2 g, b.p. 66–75° C. at 1.2 mbar. Other stannylpyridines were prepared analogously.

Precursor VP9: 5-[4-1-Amino-2-hydroxyethyl]-2-trifluoroethoxypyridine

2-Amino-2-(4-bromophenyl)ethanol VP2 (3.8 g, 17.1 mmol) and 5,5-dimethyl-2-(2-trifluoroethoxypyridin-5-yl)-1,3,2-dioxaborinane VP7 (6.55 g, 20.4 mmol) were refluxed together with tetrakis(triphenylphosphine)palladium (0.63 g, 3 mol %), sodium carbonate (3.7 g, 35.4 mmol) in toluene/ethanol/water (8:2:1, 50 ml) for 7 hours. After extractive work-up and purification by column chromatography, 5-[4-(1-amino-2-hydroxyethyl)phenyl]-2-trifluoroethoxypyridine, 2.2 g, m.p. 129° C. were obtained.

Oxazoline Products:

2-(2,6-Difluorophenyl)-4-[4-(2-ethoxypyridin-5-yl)phenyl]oxazoline (Ex. No. 2)

2-(2,6-Difluorophenyl)-4-(4-bromophenyl)oxazoline (VP4) (5.00 g, 14.8 mmol) was mixed with 2-ethoxy-5-trimethylstannylpyridine (VP8) (5.06 g, 17.8 mmol), Pd(PPh$_3$)$_4$ (0.68 g, 0.59 mmol) and lithium chloride (0.12 g, 2.9 mmol) in dioxane (40 ml) and the mixture was refluxed under nitrogen (7 hours). After extraction and chromatography, 2-(2,6-difluorophenyl)-4-[4-(2-ethoxypyridin-5-yl)phenyl]oxazoline was obtained, 3.86 g, m.p. 119° C.; $^1$H NMR (CDCl$_3$, ppm): 1.42, 4.35, OCH$_2$CH$_3$; 4.40, 4.84, 5.51, oxazoline; 6.79, 7.77, 8.36, pyridine; 7.00, 7.41, 7.54, phenyl.

2-(2,6-Difluorophenyl)-4-[4-(2-trifluoroethoxypyridin-5-yl)phenyl]oxazoline (Ex. No. 3)

2-(2,6-Difluorophenyl)-4-(4-bromophenyl)oxazoline (VP4) (2.0 g, 5.9 mmol) was mixed with 2-trifluoroethoxy-5-trimethylstannylpyridine (2.61 g, 7.7 mmol), tetrakis(triphenylphosphine)palladium (0.22 g, 0.18 mmol) and lithium chloride (0.38 g, 8.9 mmol) in dioxane (30 ml) and refluxed for 9 hours. After extractive work-up and column chromatography, 2-(2,6-difluorophenyl)-4-[4-(2-trifluoroethoxypyridin-5-yl)phenyl]oxazoline was obtained, 1.37 g, colorless crystals.

$^{19}$F NMR (CDCl$_3$): −75.05 (CF$_3$), −110.45 (ArF).

2-(2,6-Difluorophenyl)-4-[4-(2-n-propyloxypyridin-5-yl)phenyl]oxazoline (Ex. No. 4)

2-(2,6-Difluorophenyl)-4-(4-bromophenyl)oxazoline (VP4) (2.0 g, 2.9 mmol) was mixed with 2-n-propyloxy-5-trimethylstannylpyridine (4.6 g, 50%, 7.7 mmol), Pd(PPh$_3$)$_4$ (0.35 g, 0.3 mmol) and lithium chloride (50 mg) in dioxane and refluxed under nitrogen (7 hours). After chromatography and recrystallization in heptane/ethyl acetate 95:5, 2-(2,6-difluorophenyl)-4-[4-(2-n-propyloxypyridin-5-yl)phenyl]oxazoline was obtained, 1.21 g, colorless crystals;

$^1$H NMR (CDCl$_3$, ppm): 1.05, 1.82, 4.29, OC$_3$H$_7$; 4.32, 4.86, 5.51, oxazoline; 6.80, 7.78, 8.37, pyridine; 7.02, 7.42, 7.54, phenyl.

2-(2,6-Difluorophenyl)-4-[4-(2-isobutyloxypyridin-5-yl)phenyl]oxazoline (Ex. No. 8)

2-(2,6-Difluorophenyl)-4-4-bromophenyl)oxazoline (1.00 g, 2.96 mmol) was mixed with 5,5-dimethyl-2-(2-isobutyloxypyridin-5-yl)-1,3,2-dioxaborinane (1.4 g, purity 80%, 4.3 mmol), Pd(PPh$_3$)$_4$ (0.17 g, 0.15 mmol) and sodium carbonate (0.62 g, 5.9 mmol) in tolune/ethanol/water 8:2:1 (15 ml) and refluxed for 8 hours under nitrogen. After extraction and chromatography, 2-(2,6-difluorophenyl)-4-[4-(2-isobutyloxypyridin-5-yl)phenyl]oxazoline was obtained, 1.14 g, colorless oil.

$^1$H NMR (CDCl$_3$, ppm): 1.04, 2.11, 4.10, o-isobutyl; 4.33, 4.84, 5.51, oxazoline, 7.00, 7.42, 7.55, phenyl; 6.81, 7.77, 8.37, pyridine.

2-(2,6-Difluorophenyl)-4-[4-(2-trifluoroethoxypyridin-5-yl)phenyl]thiazoline (Ex. No. 19)

2-(2,6-Difluorophenyl)-4-(4-bromophenyl)thiazoline (0.90 g, 2.5 mmol, obtained from precursor VP3 and Lawesson's Reagent in toluene) was mixed with 2-trifluoroethoxy-5-trimethylstannylpyridine (1.21 g, 3.6 mmol), Pd(PPh$_3$)$_4$ (0.15 g) and lithium chloride (0.16 g) in dioxane (10 ml) and the mixture was refluxed for 8 hours. After extraction and chromatography, 2-(2,6-difluorophenyl)-4-[4-(2-trifluoroethoxypyridin-5-yl)phenyl]thiazoline was obtained, 0.46 g, beige solid; MS: M$^+$ 450.

$^1$H NMR (CDCl$_3$, ppm): 3.45, 3.94, 5.83, thiazoline; 4.82, OCH$_2$CF$_3$; 6.95, 7.87, 8.36, pyridine; 7.00, 7.40, 7.53, phenyl.

2-(2,6-Difluorophenyl)-4-[4-(2-n-propylpyridin-5-yl)phenyl]oxazoline (Ex. No. 34)

2-(2,6-Difluorophenyl)-4-(4-bromophenyl)oxazoline (0.8 g, 2.4 mmol) was refluxed for 8 hours with dimethyl-2-(2-n-propylpyridin-5-yl)-1,3,2-dioxaborinane (0.72 g, 3.1 mmol), Pd(PPh$_3$)$_4$ (0.14 g, 0.12 mmol) and sodium carbonate (0.5 g) in tolune/ethanol/water 8:2:1 (11 ml). After extraction and chromatography, 2-(2,6-difluorophenyl)-4-[4-(2-n-propylpyridin-5-yl)phenyl]oxazoline was obtained, 0.20 g, pale solid.

$^1$H NMR (CDCl$_3$, ppm): 1.01, 1.80, 2.81, n-propyl; 4.34, 4.85, 5.53, oxazoline; 7.00, 7.44, 7.59, phenyl; 7.21, 7.79, 8.76, pyridyl.

2-(2,6-Difluorophenyl)-4-[4-(2-ethylsulfinylpyridin-5-yl)phenyl]oxazoline (Ex. No. 40)

2-(2,6-Difluorophenyl)-4-[4-(2-ethylthiopyridin-5-yl)phenyl]oxazoline (Ex. No. 39; 0.60 g, 1.5 mmol) was stirred for 5 hours at 20° C. with 3-chloroperbenzoic acid (0.41 g, 1.7 mmol) in dichloroethane (10 ml). After extraction and chromatography, 2-(2,6-difluorophenyl)-4-[4-(2-ethylsulfinylpyridin-5-yl)phenyl]oxazoline was obtained, 0.21 g, colorless oil.

$^1$H NMR (CDCl$_3$, ppm): 1.24, 2.98, 3.21, SO—CH$_2$CH$_3$; 4.33, 4.87, 5.56, oxazoline; 7.01, 7.48, 7.64, phenyl; 8.03, 8.11, 8.84, pyridine.

2-(2,6-Difluorophenyl)-4-[4-(2-(N-acetylethylamino)pyridin-5-yl)phenyl]-oxazoline (Ex. No. 51)

2-(2,6-Difluorophenyl)-4-(4-trimethylstannylphenyl)oxazoline (0.84 g, 2.0 mmol) was mixed with 2-(N-acetylethylamino)-5-iodopyridine (0.93 g, 3.2 mmol), Pd(PPh$_3$)$_4$ (0.12 g) and lithium chloride (0.15 g) in dioxane (10 ml) and the mixture was refluxed for 8 hours. After separation by chromatography (eluent: ethyl acetate), 2-(2,6-difluorophenyl)-4-[4-(2-(N-acetylethylamino)pyridin-5-yl)phenyl]oxazoline was obtained, 0.31 g, pale oil.

$^1$H NMR (CDCl$_3$, ppm): 1.19, 3.94, NC$_2$H$_5$; 2.08, COCH$_3$; 4.33, 4.87, 5.54, oxazoline; 7.00, 7.43, 7.48, 7.61, phenyl; 7.32, 7.96, 8.75, pyridine.

2-(2,6-Difluorophenyl)-4-[4-(1-n-propyl-2-pyridon-5-yl)phenyl]oxazoline (Ex. No. 152)

2-(2,6-Difluorophenyl)-4-(4-trimethylstannylphenyl)oxazoline (0.5 g, 1.2 mmol) was mixed with 1-n-propyl-5-bromo-2-pyridone (0.51 g, 2.4 mmol), Pd(PPh$_3$)$_4$ (70 mg) and lithium chloride (0.20 g) in dioxane (10 ml) and refluxed for 8 hours under nitrogen. After extractive work-up and chromatography (eluent ethyl acetate), 2-(2,6-difluorophenyl)-4-[4-(1-n-propyl-2-pyridon-5-yl)phenyl]oxazoline was obtained, 0.20 g, oil.

$^1$H NMR (CDCl$_3$, ppm): 1.00, 1.81, 3.96 NC$_3$H$_7$; 4.30, 4.83, 5.49, oxazoline; 6.64, pyridone; 7.00, 7.4–7.7, phenyl and pyridone.

2-(2-Chlorophenyl)-4-[4-(2-trifluoroethoxypyridin-5-yl)phenyl]oxazoline (Ex. No. 25)

2-(2-Chlorophenyl)-4-(4-bromophenyl)oxazoline (prepared in analogy to VP4) (0.80 g, 2.4 mmol) and 5,5-dimethyl-2-(2-trifluoroethoxypyridin-5-yl)-1,3,2-dioxaborinane VP7 (1.03 g, 3.6 mmol) were refluxed with Pd(PPh$_3$)$_4$ (0.1 g) and sodium carbonate (0.5 g) in toluenelethanol/water (8:2:1, 11 ml) (8 hours). After extraction and column chromatography, 2-(2-chlorophenyl)-4-[4-(2-trifluoroethoxypyridin-5-yl)phenyl]oxazoline was obtained as a pale oil, 0.86 g;

$^1$H NMR (CDCl$_3$): 4.31, 4.80, 5.50, oxazoline; 4.80 OCH$_2$CF$_3$; 6.93, 7.3–7.5, 7.84, 8.35, pyridine and phenyl.

2-(2,6-Difluorophenyl)-4-[2-ethoxy-4-(2-trifluoroethoxypyridin-5-yl)phenyl]-oxazoline (Ex. No. 106)

Ex. 106 was prepared in analogy to Ex. No. 25.

$^1$H NMR (CDCl$_3$): 1.45, 4.15 OEt; 4.45, 4.92, 5.73, oxazoline, 4.81 OCH$_2$CF$_3$; 6.94, 7.84, 8.35, pyridine; 6.98, 7.12, 7.41, 7.53, phenyl.

2-(2-Fluorophenyl)-4-[4-(2-trifluoroethoxypyridin-5-yl)phenyl]oxazoline (Ex. No. 402)

Ex. No. 402 was prepared in analogy to Ex. No. 25.

$^1$H NMR (CDCl$_3$): 4.31, 4.82, 5.48, oxazoline; 4.80, OCH$_2$CF$_3$; 6.92, 7.84, 8.35, pyridine; 7.20, 7.40, 7.50, 8.00, phenyl.

A. CHEMICAL EXAMPLES

Tables 1–8

TABLE 1

Oxazolines and thiazolines of the formula (I), G = 3-pyridyl

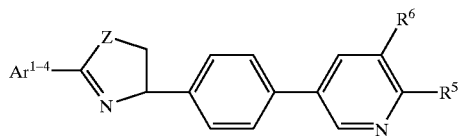

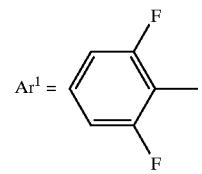

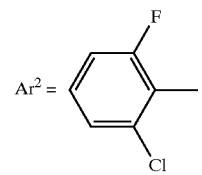

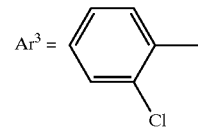

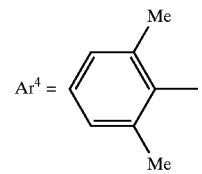

| Ex. No. | Ar | Z | $R^5$ | $R^6$ | Physical. data (m.p., MS) |
|---|---|---|---|---|---|
| 1 | $Ar^1$ | O | $OCH_3$ | H | m.p. 120° C. |
| 2 | $Ar^1$ | O | $OC_2H_5$ | H | m.p. 118° C., NMR |
| 3 | $Ar^1$ | O | $OCH_2CF_3$ | H | NMR |
| 4 | $Ar^1$ | O | $OnC_3H_7$ | H | NMR |
| 5 | $Ar^1$ | O | $OiC_3H_7$ | H | |
| 6 | $Ar^1$ | O | $OCH_2CF_2CF_2H$ | H | |
| 7 | $Ar^1$ | O | $OnC_4H_9$ | H | |
| 8 | $Ar^1$ | O | $OCH_2CH(CH_3)_2$ | H | NMR |
| 9 | $Ar^1$ | O | OsecButyl | H | |
| 10 | $Ar^1$ | O | $OnC_5H_{11}$ | H | |
| 11 | $Ar^1$ | O | $OCH(CH_3)C_3H_7$ | H | |
| 12 | $Ar^1$ | O | $OnC_6H_{13}$ | H | |
| 13 | $Ar^1$ | O | $OnC_8H_{17}$ | H | |
| 14 | $Ar^1$ | O | $OC_2H_5$ | Cl | |
| 15 | $Ar^1$ | O | $OCH_2CF_3$ | Cl | |
| 16 | $Ar^1$ | O | $OC_2H_5$ | $CH_3$ | |
| 17 | $Ar^1$ | O | $OCH_2CF_3$ | $CH_3$ | |
| 18 | $Ar^1$ | S | $OC_2H_5$ | H | |
| 19 | $Ar^1$ | S | $OCH_2CF_3$ | H | MS 450, NMR |
| 20 | $Ar^1$ | S | $OnC_3H_7$ | H | |
| 21 | $Ar^2$ | O | $OC_2H_5$ | H | |
| 22 | $Ar^2$ | O | $OCH_2CF_3$ | H | |
| 23 | $Ar^2$ | O | $OnC_3H_7$ | H | |
| 24 | $Ar^3$ | O | $OC_2H_5$ | H | |
| 25 | $Ar^3$ | O | $OCH_2CF_3$ | H | |
| 26 | $Ar^3$ | O | $OnC_3H_7$ | H | |

TABLE 1-continued

Oxazolines and thiazolines of the formula (I), G = 3-pyridyl

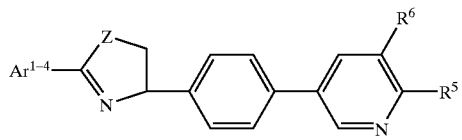

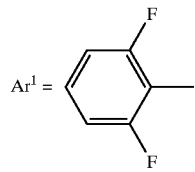

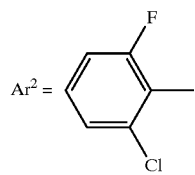

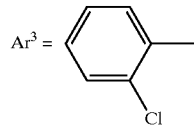

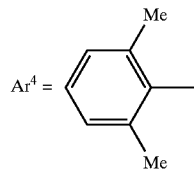

| Ex. No. | Ar | Z | R⁵ | R⁶ | Physical. data (m.p., MS) |
|---|---|---|---|---|---|
| 27 | Ar⁴ | O | OC₂H₅ | H | |
| 28 | Ar⁴ | O | OCH₂CF₃ | H | Smp.: 136–137° C. 1H-NMR (CDCl3, TMS): δ = 2.46 (s,6H,CH3); 4.33, 4.88, 5.57 (each dd, 1H, Oxazolin); 4.85 8q, 2H, CH2CF3); 6.97, 7.90, 8.39 (each dd, 1H, PyH); 7.59, 7.51 (each m, 2H, C6H4); 7.08–7.28 (m, 3H, C6H3). 19F-NMR (CDCl3, CFCl3): δ = −74.3 |
| 29 | Ar⁴ | O | OnC₃H₇ | H | |
| 30 | Ar¹ | O | OCH(CF₃)CH₂OCH₃ | H | |
| 31 | Ar¹ | O | CH₃ | H | |
| 32 | Ar¹ | O | CF₃ | H | |
| 33 | Ar¹ | O | C₂H₅ | H | |
| 34 | Ar¹ | O | nC₃H₇ | H | |
| 35 | Ar¹ | O | nC₄H₉ | H | m.p. 117° C. |
| 36 | Ar¹ | O | nC₅H₁₁ | H | |
| 37 | Ar¹ | O | nC₆H₁₃ | H | |
| 38 | Ar¹ | O | SCF₃ | H | |
| 39 | Ar¹ | O | SC₂H₅ | H | m.p. 100° C. |
| 40 | Ar¹ | O | SO—C₂H₅ | H | |
| 41 | Ar¹ | O | SO₂—C₂H₅ | H | |
| 42 | Ar¹ | O | SCH₂CF₃ | H | |
| 43 | Ar¹ | O | S-nC₃H₇ | H | m.p. 90° C. |
| 44 | Ar¹ | O | SO-nC₃H₇ | H | |
| 45 | Ar¹ | O | SO₂-nC₃H₇ | H | |
| 46 | Ar¹ | O | S-nC₄H₉ | H | |
| 47 | Ar¹ | O | Br | H | MS 414, 416 |
| 48 | Ar¹ | O | Cl | Cl | |

TABLE 1-continued

Oxazolines and thiazolines of the formula (I), G = 3-pyridyl

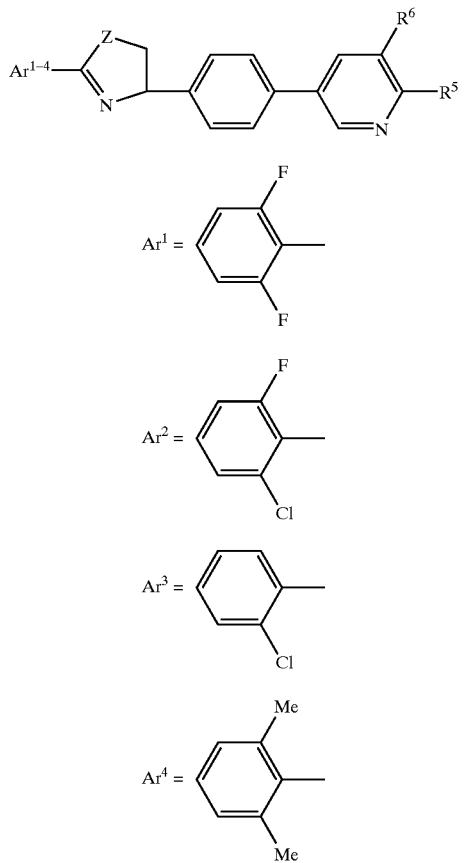

| Ex. No. | Ar | Z | R⁵ | R⁶ | Physical. data (m.p., MS) |
|---|---|---|---|---|---|
| 49 | Ar¹ | O | NH—COCH₃ | H | |
| 50 | Ar¹ | O | NH—COC₂H₅ | H | |
| 51 | Ar¹ | O | N(C₂H₅)COCH₃ | H | NMR |
| 52 | Ar¹ | O | 1-Morpholinyl | H | m.p. 170° C. |
| 53 | Ar¹ | O | CH₂OCH₃ | H | |
| 54 | Ar¹ | O | CH₂OC₂H₅ | H | |
| 55 | Ar¹ | O | C₂H₄OCH₃ | H | |
| 56 | Ar¹ | O | OCH₂C₆H₅ | H | m.p. 120° C. |
| 57 | Ar¹ | O | OCH₂CON(CH₃)₂ | H | |
| 58 | Ar¹ | O | OC₂H₄CH(CH₃)₂ | H | |
| 59 | Ar¹ | O | OCH₂CH(C₂H₅)CH₃ | H | |
| 60 | Ar¹ | O | OCH₂—COOCH₃ | H | |
| 61 | Ar¹ | O | OCHF₂ | H | ¹⁹F NMR: −90.1, d; −110.5, ArF |
| 62 | Ar¹ | O | OCH₂CHF₂ | H | |
| 63 | Ar¹ | O | OCH(CH₃)CF₃ | H | |
| 64 | Ar¹ | O | OC₃H₆CF₃ | H | |
| 65 | Ar¹ | O | OCH₂C₂F₅ | H | |
| 66 | Ar¹ | O | C₂H₄OC₂H₅ | H | |
| 67 | Ar¹ | O | N(CH₃)C₂H₅ | H | |
| 68 | Ar¹ | O | N(CH₃)nC₃H₇ | H | |
| 69 | Ar¹ | O | NHnC₃H₇ | H | |
| 70 | Ar¹ | O | NHnC₄H₉ | H | |
| 71 | Ar¹ | O | N(C₂H₅)₂ | H | |
| 72 | Ar¹ | O | 1-Piperidinyl | H | |
| 73 | Ar¹ | O | SO—CF₃ | H | |
| 74 | Ar¹ | O | SCHF₂ | H | |
| 75 | Ar¹ | O | SO—CHF₂ | H | |
| 76 | Ar¹ | O | SO—CH₂CF₃ | H | |
| 77 | Ar¹ | O | SO₂—CH₂CF₃ | H | |
| 78 | Ar¹ | O | SO₂—CF₃ | H | |

TABLE 1-continued

Oxazolines and thiazolines of the formula (I), G = 3-pyridyl

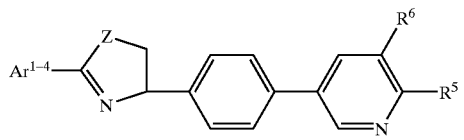

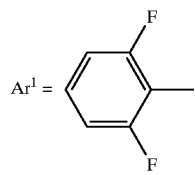

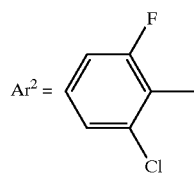

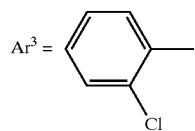

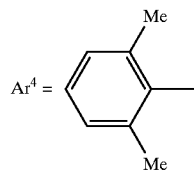

| Ex. No. | Ar | Z | $R^5$ | $R^6$ | Physical. data (m.p., MS) |
|---|---|---|---|---|---|
| 79 | $Ar^1$ | O | $SO_2$—$CHF_2$ | H | |
| 80 | $Ar^1$ | O | $SCH_3$ | H | |
| 81 | $Ar^1$ | O | SO—$CH_3$ | H | |
| 82 | $Ar^1$ | O | $SO_2$—$CH_3$ | H | |
| 83 | $Ar^1$ | O | $C_2H_4CF_3$ | H | |
| 84 | $Ar^1$ | O | $CH_2CF_3$ | H | |
| 85 | $Ar^1$ | O | $cC_5H_9$ | H | |
| 86 | $Ar^1$ | O | $CH_2cC_6H_{11}$ | H | |
| 87 | $Ar^1$ | O | CN | H | |
| 88 | $Ar^1$ | O | $OC_6H_5$ | H | |
| 89 | $Ar^1$ | O | $CH_2C_6H_5$ | H | |
| 90 | $Ar^1$ | O | $4(OCF_3)$—$C_6H_4$ | H | |
| 91 | $Ar^1$ | O | $OCH_2CF_3$ | CN | |
| 92 | $Ar^1$ | O | $OCH_2CF_3$ | $SCH_3$ | |
| 93 | $Ar^1$ | O | $R^5 + R^6 = $—$C^3H_6O$— | | |
| 94 | $Ar^1$ | O | $R^5 + R^6 = $—$OC_2H_4O$— | | |
| 95 | $Ar^3$ | O | $SCF_3$ | H | |
| 96 | $Ar^3$ | O | $OCHF_2$ | H | |
| 97 | $Ar^3$ | O | $OCF_2CF_2H$ | H | |

TABLE 2

Oxazolines of the formula (I), G = 3-pyridyl

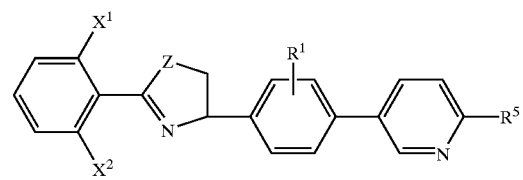

| Ex. No. | $X^1$ | $X^2$ | Z | E | $R^1$ | $R^5$ | physical data |
|---|---|---|---|---|---|---|---|
| 100 | F | F | O | $CH_2$ | H | $OC_2H_5$ | m.p. 105° C. |
| 101 | F | F | O | $CH_2$ | H | $OCH_2CF_3$ | |
| 102 | F | F | O | $CH_2$ | H | $OnC_3H_7$ | |
| 103 | F | F | O | — | 2-F | $OC_2H_5$ | |
| 104 | F | F | O | — | 2-Cl | $OCH_2CF_3$ | |
| 105 | F | F | O | — | 2-$OCH_3$ | $OC_2H_5$ | |
| 106 | F | F | O | — | 2-$OC_2H_5$ | $OCH_2CF_3$ | NMR |
| 107 | F | F | O | — | 3-Cl | $OnC_3H_7$ | |
| 108 | F | F | O | — | 2-F | $OCH_2CF_3$ | |
| 109 | F | F | O | — | 2-Cl | $OC_2H_5$ | |
| 110 | F | F | O | — | 2-$OCH_3$ | $OCH_2CF_3$ | |
| 111 | F | F | O | — | 2-$OC_2H_5$ | $OC_2H_5$ | |
| 112 | F | F | O | — | 2-$OCH_3$ | $OnC_3H_7$ | |
| 113 | F | F | O | — | 2-$OC_2H_5$ | $OnC_3H_7$ | |
| 114 | F | F | O | — | 3-F | $OC_2H_5$ | |
| 115 | F | Cl | O | — | 2-$OCH_3$ | $OC_2H_5$ | |
| 116 | Br | H | O | — | H | $OC_2H_5$ | |
| 117 | Br | H | O | — | H | $OCH_2CF_3$ | |
| 118 | I | H | O | — | H | $OnC_3H_7$ | |
| 119 | F | H | O | — | H | $OCH_2CF_3$ | |
| 120 | $CF_3$ | H | O | — | H | $OC_2H_5$ | |
| 121 | $OCH_3$ | H | O | — | H | $OnC_3H_7$ | |
| 122 | CN | H | O | — | H | $OC_2H_5$ | |
| 123 | $OCHF_2$ | H | O | — | H | $OC_2H_5$ | |
| 124 | $C_2H_5$ | H | O | — | H | $OC_2H_5$ | |
| 125 | $OCH_3$ | F | O | — | H | $OC_2H_5$ | |
| 126 | F | H | O | — | H | $OC_2H_5$ | |
| 127 | $OCH_3$ | F | O | — | H | $OCH_2CF_3$ | |
| 128 | $CF_3$ | H | O | — | H | $OCH_2CF_3$ | |
| 129 | $CH_3$ | H | O | — | H | $OC_2H_5$ | |
| 130 | $CH_3$ | H | O | — | H | $OCH_2CF_3$ | |
| 131 | F | F | O | — | $CH_3$ | $OC_2H_5$ | |
| 132 | F | F | O | — | $C_2H_5$ | $OC_2H_5$ | |
| 133 | F | F | O | — | $OCHF_2$ | $OC_2H_5$ | |
| 134 | F | F | O | $CH_2O$ | H | $OC_2H_5$ | |

TABLE 3

Oxazolines of the formula (I), G = 2-pyridon-5-yl

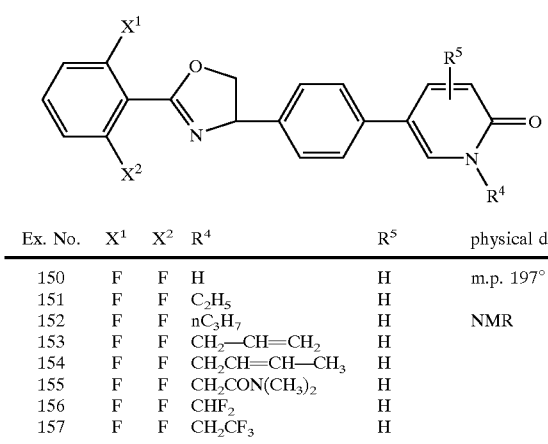

| Ex. No. | $X^1$ | $X^2$ | $R^4$ | $R^5$ | physical data |
|---|---|---|---|---|---|
| 150 | F | F | H | H | m.p. 197° C. |
| 151 | F | F | $C_2H_5$ | H | |
| 152 | F | F | $nC_3H_7$ | H | NMR |
| 153 | F | F | $CH_2$—CH=$CH_2$ | H | |
| 154 | F | F | $CH_2CH$=CH—$CH_3$ | H | |
| 155 | F | F | $CH_2CON(CH_3)_2$ | H | |
| 156 | F | F | $CHF_2$ | H | |
| 157 | F | F | $CH_2CF_3$ | H | |

TABLE 3-continued

Oxazolines of the formula (I), G = 2-pyridon-5-yl

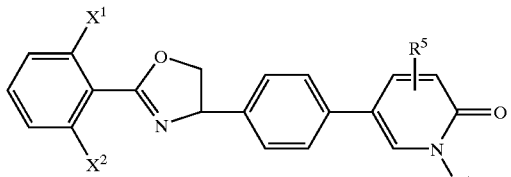

| Ex. No. | $X^1$ | $X^2$ | $R^4$ | $R^5$ | physical data |
|---|---|---|---|---|---|
| 158 | F | F | $CH_2C_6H_5$ | H | |
| 159 | F | F | $CH_2CH(CH_3)_2$ | H | |
| 160 | F | F | $CH_2$—CCH | H | |
| 161 | F | F | $CH_2$—CC—$CH_3$ | H | |
| 162 | F | F | $cC_6H_{11}$ | H | |
| 162 | F | F | $cC_5H_9$ | H | |
| 163 | F | F | $CH_2cC_6H_{11}$ | H | |
| 164 | F | F | $C_2H_4OC_2H_5$ | H | |
| 165 | F | F | $CH_2OCH_2C_6H_5$ | H | |
| 166 | F | F | $C_2H_5$ | 3-Cl | |
| 167 | F | F | $nC_3H_7$ | 3-Cl | |
| 168 | F | F | $C_2H_5$ | 3-$CH_3$ | |
| 169 | F | F | $nC_3H_7$ | 3-$CH_3$ | |

TABLE 4

Oxazolines of the formula (I), G = 4-pyridyl

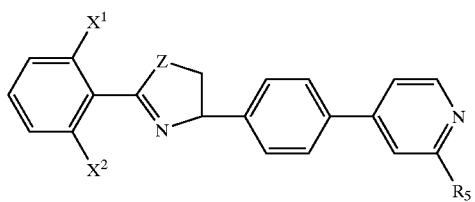

| Ex. No. | $X^1$ | $X^2$ | Z | $R^5$ | physical data |
|---|---|---|---|---|---|
| 170 | F | F | O | H | m.p. 137° C. |
| 171 | F | F | O | $OC_2H_5$ | |
| 172 | F | F | O | Cl | |
| 173 | F | Cl | O | $OC_2H_5$ | |
| 174 | F | F | O | $C_2H_5$ | |
| 175 | F | F | O | $nC_4H_9$ | |
| 176 | F | F | O | $OCH_2CF_3$ | |
| 177 | F | F | O | $CF_3$ | |
| 178 | F | F | O | $OnC_3H_7$ | |
| 179 | F | F | O | $SC_2H_5$ | |
| 180 | F | F | O | SO—$C_2H_5$ | |
| 181 | F | F | O | $SO_2$—$C_2H_5$ | |
| 182 | F | F | S | $OC_2H_5$ | |
| 183 | F | F | S | $OnC_3H_7$ | |
| 184 | F | F | O | $OCH_2$-3-Pyridyl | |
| 185 | F | F | O | 1-Pyrrolyl | |
| 186 | F | F | O | (tetrahydrofuranylmethoxy) | |

TABLE 5

Oxazolines of the formula (I), G = 2-Pyridon-3-yl

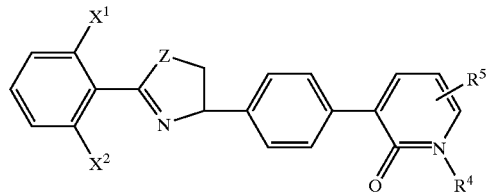

| Ex. No. | $X^1$ | $X^2$ | Z | $R^4$ | $R^5$ | physical data |
|---|---|---|---|---|---|---|
| 200 | F | F | O | $C_2H_5$ | H | |
| 201 | F | F | O | $C_2H_5$ | 6-$OC_2H_5$ | |
| 202 | F | F | O | $C_2H_5$ | 6-$OCH_2CF_3$ | |
| 203 | F | F | O | $C_2H_5$ | 6-$OnC_3H_7$ | |
| 204 | F | F | O | $CH_3$ | H | |
| 205 | F | F | O | $CH_3$ | 6-$OC_2H_5$ | |
| 206 | F | F | O | $CH_3$ | 6-$OCH_2CF_3$ | |
| 207 | F | F | O | $CH_3$ | 6-$OnC_3H_7$ | |
| 208 | F | F | O | $CH_3$ | 5-Cl | |
| 209 | F | F | O | $CH_3$ | 5-Br | |
| 210 | F | F | O | $CH_2CF_3$ | H | |
| 211 | F | F | O | $CH_2CF_3$ | 6-$OC_2H_5$ | |

TABLE 6

Oxazolines of the formula (I), G = 2-pyridon-4-yl

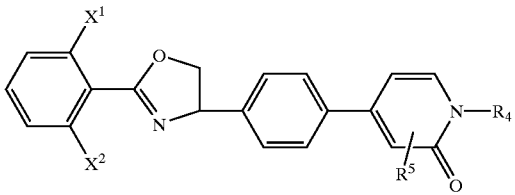

| Ex. No. | $X^1$ | $X^2$ | $R^4$ | $R^5$ | physical data |
|---|---|---|---|---|---|
| 250 | F | F | $CH_3$ | H | |
| 251 | F | F | $C_2H_5$ | H | |
| 252 | F | F | $CH_2CF_3$ | H | |
| 253 | F | F | $nC_3H_7$ | H | |
| 254 | F | F | $iC_3H_7$ | H | |
| 255 | F | F | $nC_4H_9$ | H | |
| 256 | F | F | $CH_2CH(CH_3)_2$ | H | |
| 257 | F | F | $CH_2C_6H_5$ | H | |
| 258 | F | F | $CH_2cC_6H_{11}$ | H | |
| 259 | F | F | $C_2H_4OCH_3$ | H | |
| 260 | F | F | $C_2H_4OC_2H_5$ | H | |
| 261 | F | F | $C_2H_5$ | 5-Cl | |

TABLE 7

Oxazolines of the formula (I), G = 3-pyridinyl, Ar = heteroaryl

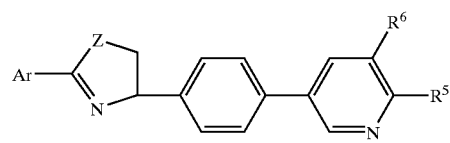

| Ex. No. | Ar | Z | $R^5$ | $R^6$ | physical data |
|---|---|---|---|---|---|
| 300 | 3-Cl-2-methylpyridin-yl | O | $OC_2H_5$ | H | |
| 301 | 3-Cl-2-methylpyridin-yl | O | $OCH_2CF_3$ | H | |
| 302 | 3-F-2-methylpyridin-yl | O | $OC_2H_5$ | H | |

TABLE 7-continued

Oxazolines of the formula (I), G = 3-pyridinyl, Ar = heteroaryl

| Ex. No. | Ar | Z | R⁵ | R⁶ | physical data |
|---|---|---|---|---|---|
| 303 | 3-fluoro-2-methylpyridin-2-yl (F, pyridine with methyl) | O | OCH$_2$CF$_3$ | H | |
| 304 | 2-chloro-3-methylpyridin-3-yl | O | OC$_2$H$_5$ | H | |
| 305 | 3-methylpyridin-3-yl | O | OC$_2$H$_5$ | H | |
| 306 | 3,4-dimethylpyridin-3-yl (CH$_3$) | O | OC$_2$H$_5$ | H | |
| 307 | 3,4-dimethylpyridin-3-yl (CH$_3$) | O | OCH$_2$CF$_3$ | H | |
| 308 | 5-chloro-1,3,4-trimethylpyrazol-3-yl | O | OC$_2$H$_5$ | H | |
| 309 | 5-chloro-1,3,4-trimethylpyrazol-3-yl | O | OCH$_2$CF$_3$ | H | |
| 310 | 1,3-dimethyl-4,5,6,7-tetrahydroindazol-3-yl | O | OC$_2$H$_5$ | H | |

TABLE 7-continued

Oxazolines of the formula (I), G = 3-pyridinyl, Ar = heteroaryl

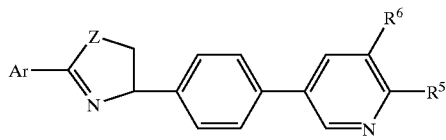

| Ex. No. | Ar | Z | $R^5$ | $R^6$ | physical data |
|---|---|---|---|---|---|
| 311 | (1,3-dimethyl-4,5,6,7-tetrahydroindazol-3-yl) | O | $OCH_2CF_3$ | H | |
| 312 | (4-methylpyrimidin-5-yl) | O | $OCH_2CF_3$ | H | |
| 313 | (pyrazin-2-yl) | O | $OC_2H_5$ | H | |
| 314 | (3-chlorothien-2-yl) | O | $OC_2H_5$ | H | |
| 315 | (4-trifluoromethylpyridin-3-yl) | O | $OCH_2CF_3$ | H | $^{19}F$ NMR: −62.3, s, −74.3, tr |

TABLE 8

Oxazolines of the formula I, G = 3-pyridinyl

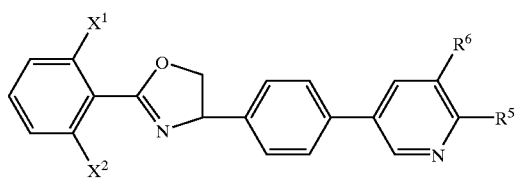

$R^5$ = heterocyclyl, heterocyclyloxy, heterocyclylalkyl, heterocyclylalkoxy

| Ex. No. | $X^1$ | $X^2$ | $R^6$ | $R^5$ | physical data |
|---|---|---|---|---|---|
| 350 | F | F | H |  | |

TABLE 8-continued

Oxazolines of the formula I, G = 3-pyridinyl

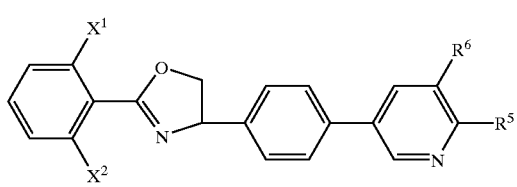

$R^5$ = heterocyclyl, heterocyclyloxy, heterocyclylalkyl, heterocyclylalkoxy

| Ex. No. | $X^1$ | $X^2$ | $R^6$ | $R^5$ | physical data |
|---|---|---|---|---|---|
| 351 | F | F | H |  | |

TABLE 8-continued
Oxazolines of the formula I, G = 3-pyridinyl
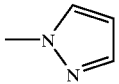
R⁵ = heterocyclyl, heterocyclyloxy, heterocyclylalkyl, heterocyclylalkoxy
| Ex. No. | X¹ | X² | R⁶ | R⁵ | physical data |
|---|---|---|---|---|---|
| 352 | F | F | H | 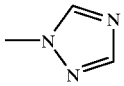 | |
| 353 | F | F | H | 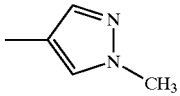 | |
| 354 | F | F | H | 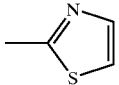 | |
| 355 | F | F | H | 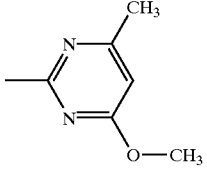 | |
| 356 | F | F | H | 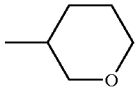 | |
| 357 | F | F | H | 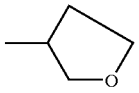 | |
| 358 | F | F | H | 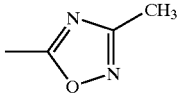 | |
| 359 | F | F | H | 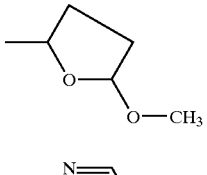 | |
| 360 | F | F | H | 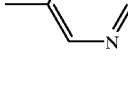 | |
| 361 | F | F | H | 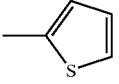 | |
| 362 | F | F | H | 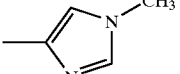 | |
| 363 | F | F | H | 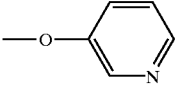 | |
| 364 | F | F | H | 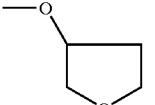 | |
| 365 | F | F | H | 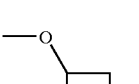 | |
| 366 | F | F | H | 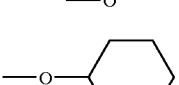 | |
| 367 | F | F | H | 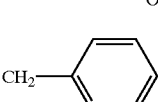 | |
| 369 | F | F | H | 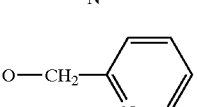 | |
| 370 | F | F | H | 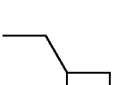 | |
| 371 | F | F | H | 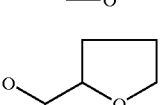 | |
| 372 | F | F | H | 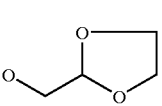 | |
| 373 | F | F | H | | |

TABLE 8-continued

Oxazolines of the formula I, G = 3-pyridinyl $R^5$ = heterocyclyl, heterocyclyloxy, heterocyclylalkyl, heterocyclylalkoxy

| Ex. No. | $X^1$ | $X^2$ | $R^6$ | $R^5$ | physical data |
|---|---|---|---|---|---|
| 374 | F | F | H | 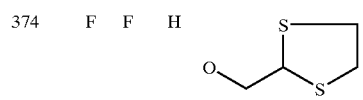 | |
| 375 | F | F | H | 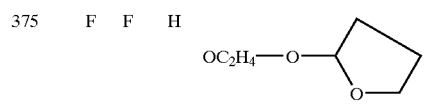 | |
| 376 | F | F | H | 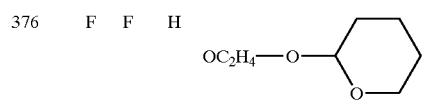 | |
| 377 | F | F | H | 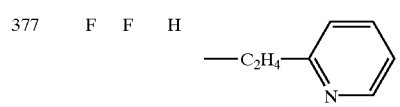 | |
| 378 | F | F | H | 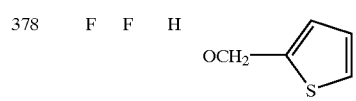 | |
| 379 | F | F | H | 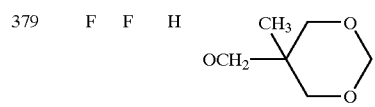 | |
| 380 | F | F | H | 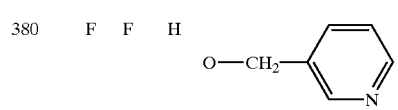 | |
| 381 | F | F | H | 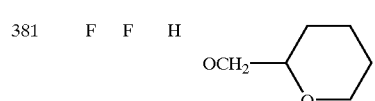 | |
| 382 | F | F | H | 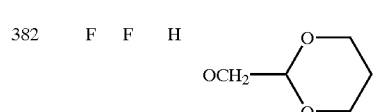 | |
| 383 | F | F | H | 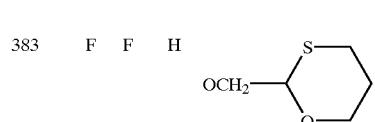 | |

TABLE 9

Oxazolines of the formula (I), G = 3-pyridinyl

| Ex. No. | $X^1$ | $X^2$ | $R^6$ | $R^5$ | physical data |
|---|---|---|---|---|---|
| 400 | 2-F | 4-F | H | $OCH_2CF_3$ | $^{19}$F NMR: −75.1, tr, $CF_3$, −105.4, m, ArF |
| 401 | 2-F | 5-F | H | $OCH_2CF_3$ | $^{19}$F NMR: −74.3, $CF_3$; −115.1, −118.7, ArF |
| 402 | 2-F | | H | $OCH_2CF_3$ | NMR, m.p. 101° C. |
| 403 | 2-$CH_3$ | H | H | $OCH_2CF_3$ | oil, $^1$H-NMR ($CDCl_3$, TMS): δ = 2.67 (s, 3H, $CH_3$); 4.24, 4.78, 5.48 (each dd, 1H, Oxazolin), 4.81 (q, 2H, $CH_2CF_3$), 6.93, 8.35 (each d, 1H, PyH), 7.84 (dd, 1H, PyH); 7.52, 7.42 (each m, 2H, $C_6H_4$); 7.91 (d, 1H, $MeC_6H_4$), 7.2–7.4 (m, 3H, $MeC_6H_4$). $^{19}$F-NMR ($CDCl_3$, $CFCl_3$): δ = −74.3 |
| 404 | 2-$CH_3$ | H | H | $OCH_2CF_3$ | |
| 405 | 2-$CH_3$ | H | H | $OnC_3H_7$ | |
| 406 | 2-Et | H | H | $OCH_2CF_3$ | |
| 407 | 2-$CH_3$ | 4-$CH_3$ | H | $OCH_2CF_3$ | |
| 408 | 2-F | 4-$CH_3$ | H | $OCH_2CF_3$ | |
| 409 | 2-F | 4-Cl | H | $OCH_2CF_3$ | |
| 410 | 2-$SCH_3$ | H | H | $OCH_2CF_3$ | |
| 411 | 2-$OC_2H_5$ | H | H | $OCH_2CF_3$ | |
| 412 | 2-$OCH_3$ | H | H | $OCH_2CF_3$ | oil, $^1$H-NMR ($CDCl_3$, TMS): δ = 3.97 (s, 3H, $OCH_3$); 4.30, 4.80, 5.50 (each dd, 1H, Oxazolin); 4.84 (q, 2H, $CH_2CF_3$); 6.95, 7.90, 8.37 (each dd, 1H, PyH); 7.46, 7.54 (each m, 2H, $C_6H_4$); 7.0–7.08 (m, 2H, $MeOC_6H_4$), 7.43–7.58 (m, 1H, $MeOC_6H_4$), 7.87 (dd, 1H, $MeOC_6H_4$). $^{19}$F-NMR ($CDCl_3$, $CFCl_3$): δ = −74.3 |

B. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexanone as solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and these are dried and mixed intimately. The wettable powder amounts to approx. 5% by weight and the inert carrier material to approx. 95% by weight of the finished granules.

C. BIOLOGICAL EXAMPLES

Example 1

Effect on the Spider Mites Tetranychus urticae

Bean plants (Phaseolus vulgaris) which were severely infested with a complete population of spider mites (Tetranychus urticae) were sprayed to runoff point with an aqueous solution of the formulated preparation to be tested. The mortality of all mite stages was determined after 7 days. At a concentration of 300 ppm (based on active substance content), a 90–100% mortality was shown by the preparations of Examples 1, 2, 3, 4, 7, 8, 9, 14, 18, 21, 31, 40, 41, 43, 44, 47, 51, 106, 152 and 153.

Example 2

Effect on the Aphid Aphis fabae

Field beans (Vicia faba) which were densely populated with the black bean aphid (Aphis fabae) were sprayed to runoff point with an aqueous solution of the formulated preparation to be tested. The mortality of the aphids was determined after 3 days. At a concentration of 300 ppm (based on the active substance content), a 90–100% mortality was shown by the preparations of Examples 1, 2, 3, 4, 7, 8, 152.

Example 3

Effect on the Butterfly Larva Spodoptera litoralis

Ten L4 larvae of the Egyptian cotton leafworm (Spodoptera litoralis) were introduced into a Petri dish whose bottom was covered with filter paper and contained approx. 5 ml of nutrient medium. Filter paper, nutrient paper and the larvae which had been introduced were then sprayed with an aqueous solution of the formulated preparation to be tested. The Petri dish was subsequently sealed with a lid. After 4 days' storage at approx. 23° C., the effect of the preparation on the larvae was determined. At a concentration of 300 ppm (based on the active substance content), a 90–100% larval mortality was caused by the preparations of Examples 3, 4, 22, 105, 106.

Example 4

Effect on the Egg-Larval Stage of Heliothis virescens

A Petri dish whose bottom was covered with filter paper and which contained approx. 5 ml of nutrient medium was prepared. Filter paper sections containing approx. 30 24-hour-old eggs of the tobacco budworm (Heliothis virescens) were immersed for 5 seconds into an aqueous solution of the formulated preparation to be tested and subsequently placed in the Petri dish. A further 200 μl of the aqueous solution were distributed over the nutrient medium. After the Petri dish had been sealed, it was stored in a controlled-environment cabinet at approx. 25° C. After 6 days' storage, the mortality of the preparation on the eggs and any larvae hatched from them was determined. At a concentration of 300 ppm (based on the active substance content), a 90–100% mortality was caused by the preparations of Examples 1, 2, 3, 4, 5, 6, 7, 8, 14, 17, 21, 22, 23, 34, 35, 39, 40, 43, 44, 106.

Example 5

Effect on the Corn Budworm Diabrotica undecimpunctata

Maize seed was pregerminated for 6 hours while submerged in water, then placed into 10-ml glass tubes and covered with 2 ml of soil in each case. After 1 ml of water had been added, the plants remained in the glass tubes at 21° C. until plant length was approx. 3 cm. 10 L2 larvae of the corn budworm (Diabrotica undecimpunctata) were then introduced into each tube on the soil. Two hours later, 1 ml of an aqueous solution of the formulated preparation to be tested were pipetted onto the soil surface in the tubes. After storage for 5 days under laboratory conditions at 21° C., the soil and root sections were examined for live Diabrotica larvae and the mortality was determined. At a concentration of 300 ppm (based on the active substance content), a 100% mortality of the test animals employed was shown by the preparations of Example 2, 3, 5, 9, 19, 39.

Example 6

Effect on the Larvae of the Copperbottle Lucilia cuprina

In a sample container, 20 recently hatched larvae of the copperbottle Lucilia cuprina were placed on a larval nutrient medium of ground mutton which contained the test substance in a concentration of 100 ppm. Larval growth on the nutrient medium is monitored over 72 hours up to larva 3. At a concentration of 100 ppm (based on the active substance content), a 100% mortality in the fly larvae employed was shown by the preparations of Examples 2, 3, 4, 5, 105, 106.

Example 7

Effect on Developmental Stages of the Cat Flea Ctenocephalides felis

The larval nutrient medium of the cat flea, composed of equal parts of blood meal and quartz sand, was admixed with the test substance at a concentration of 1000 ppm. Approx. 30 flea eggs freshly obtained from a breeding colony were transferred onto the medium. To assess the affect of the preparation, hatching of the flea larvae and their development into pupae and adult fleas was observed. A mortality of 100% was caused by the test substances of Examples 2, 3 and 4.

What is claimed is:

1. A compound of the formula:

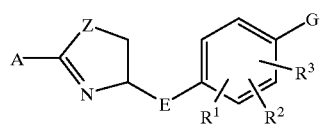

(I)

in which

A is phenyl pyridyl, pyrimidinyl, pyrazinyl, pyrazolyl or thienyl, each of the abovementioned groups are optionally substituted by one or more radicals X;

X is identical or different
a) halogen, cyano, nitro;
b) $(C_1-C_4)$alkyl, $(C_2-C_4)$alkenyl, $(C_2-C_4)$alkynyl, $(C_1-C_4)$alkoxy, $(C_1-C_4)$alkylthio, $(C_1-C_4)$alkylsulfinyl, $(C_3-C_8)$cycloalkyl, $(C_4-C_8)$cycloalkenyl, phenyl,
the radicals of group b are optionally substituted by one or more radicals selected from the group consisting of halogen, cyano, $(C_1-C_4)$alkyl, $(C_1-C_4)$haloalkyl, $(C_1-C_4)$alkoxy and $(C_1-C_4)$ haloalkoxy;

E is a single bond, $(C_1-C_4)$alkylene, —O—$CH_2$— or —$CH_2$—O—;

G is a radical selected from the group consisting of:

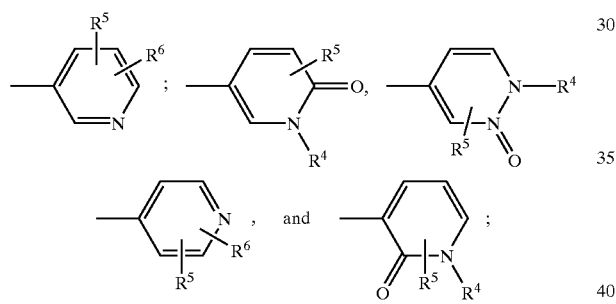

Z is oxygen or sulfur;

$R^1$, $R^2$ and $R^3$ are identical or different hydrogen, halogen, $(C_1-C_4)$haloalkyl, $(C_1-C_4)$alkyl, $(C_1-C_4)$alkoxy, $(C_1-C_4)$haloalkoxy or cyano;

$R^4$ is hydrogen or a group $(C_1-C_8)$alkyl, $(C_2-C_8)$alkenyl, $(C_2-C_8)$alkynyl, $(C_3-C_8)$cycloalkyl, $(C_3-C_8)$cycloalkenyl, $(C_4-C_{10})$cycloalkylalkyl, or $(C_7-C_{12})$phenylalkyl, each of the above-mentioned groups are optionally substituted by one or more substituents from the group consisting of halogen, $(C_1-C_4)$alkyl, $(C_1-C_4)$haloalkyl, $(C_1-C_4)$alkoxy, $(C_1-C_3)$haloalkoxy, $(C_1-C_3)$alkylthio, $(C_3-C_8)$cycloalkyl, $(C_7-C_{12})$phenylalkoxy, $(C_2-C4)$alkylcarbonyl, alkoxycarbonyl, $(C_2-C_8)$ monoalkyl- and $(C_3-C_9)$dialkylaminocarbonyl, cyano and tri$(C_1-C_4)$alkylsilyl;

$R^5$ and $R^6$ are identical or different
a) hydrogen, halogen, cyano, formyl, $(C_2-C_5)$ alkylcarbonyl, $(C_2-C_8)$alkoxylcarbonyl, $(C_3-C_9)$ monoalkyl- and dialkylaminocarbonyl;
b) $(C_1-C_8)$alkyl, $(C_3-C_8)$cycloalkyl, $(C_4-C_8)$ cycloalkenyl, $(C_1-C_8)$alkoxyalkyl, $(C_1-C_8)$ alkylthio, $(C_1-C_8)$alkylsulfinyl, $(C_1-C_8)$ alkylsulfonyl, $NR^7R^8$, phenyl, phenoxy, $(C_7-C_{12})$ phenylalkyl, $(C_7-C_{12})$phenylalkoxy, heterocyclyl, heterocyclyloxy derivatives heterocyclyl$(C_1-C_4)$alkoxy, $(C_3-C_{12})$ heterocyclylalkyl, each of the group b radicals are optionally substituted by one or more radicals selected from the group consisting of halogen, $(C_1-C_4)$alkyl, $(C_1-C_3)$haloalkyl, $(C_1-C_3)$alkoxy, $(C_1-C_3)$haloalkoxy, $(C_1-C_3)$alkylthio, $NR^7R^8$, alkylcarbonyl$(C_2-C_5)$, alkoxycarbonyl $(C_2-C_8)$, monoalkyl- and dialkylaminocarbonyl $(C_3-C_9)$, cyano and tri$(C_1-C_4)$alkylsilyl,
c) $(C_1-C_8)$alkoxy, which is optionally substituted by one or more radicals selected from the group consisting of halogen, $(C_1-C_3)$alkylthio, $NR^7R^8$, alkylcarbonyl$(C_2-C_5)$, alkoxycarbonyl, $(C_2-C_8)$, monoalkyl- and dialkylaminocarbonyl $(C_3-C_9)$, cyano and tri$(C_1-C_4)$alkylsilyl,
d) $R^5$ and $R^6$ together form $(C_3-C_8)$alkylene, a $(C_4-C_8)$ alkenylene, a $(C_7-C_{12})$phenylalkylene, a $(C_2-C_4)$ alkyleneoxy, a $(C_1-C_2)$alkylenedioxy, a $(C_2-C_4)$ alkyleneamino or a $(C_2-C_4)$alkylenethio ring, $R^7$ and $R^8$ are identical or different
a) hydrogen;
b) $(C_1-C_8)$alkyl, $(C_3-C_8)$cycloalkyl, $(C_7-C_{12})$ phenylalkyl, $(C_1-C_6)$alkycarbonyl, $(C_1-C_6)$ alkylsulfonyl which are optionally substituted by one or more radicals selected from the group consisting of halogen, $(C_1-C_4)$alkyl, $(C_1-C_3)$haloalkyl, $(C_1-C_4)$alkoxy, $(C_1-C_3)$haloalkoxy, $(C_1-C_3)$ alkylthio, $(C_1-C_3)$alkylamino, $(C_1-C_3)$ dialkylamino, $(C_3-C_8)$cycloalkyl, cyano and tri $(C_1-C_4)$alkylsilyl or $R^7$ and $R^8$ together are alkylene $(C_3-C_7)$, $(C_3-C_7)$oxa-, aza- or thiaalkylene, $(C_3-C_7)$ alkylenecarbonyl or $(C_3-C_7)$alkylenesulfonyl
provided that when Z is oxygen, either $R^5$ and $R^6$ are heterocyclyl, heterocyclyl derivative, heterocyclyl $(C_1-C_4)$alkoxy or $(C_3-C_{12})$ heterocyclyloxy or $R^7$ and $R^8$ together are alkylene $(C_3-C_7)$, $(C_3-C_2)$oxa- aza- or thiaalkylene, $(C_3-C_7)$alkylenecarbonyl or $(C_3-C_7)$alkylenesulfonyl, and
wherein the heterocycle in the heterocycle, heterocyclyloxy, heterocyclyl $(C_1-C_4)$alkoxy or the $(C_3-C_{12})$ heterocyclylalkyl group is selected from the group consisting of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b] thiophene, benzo[b]furan, indole, benzo[c] thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine and 4H-quinolizine.

2. The compound as claimed in claim 1, where

A is phenyl or pyridyl;

X is
a) halogen, cyano, nitro; or
b) $(C_1-C_4)$alkyl, $(C_1-C_4)$alkenyl, $(C_1-C_4)$alkynyl, $(C_1-C_4)$alkoxy, $(C_1-C_4)$alkylthio, $(C_1-C_4)$ alkylsulfinyl, $(C_3-C_7)$cycloalkyl, $(C_4-C_8)$ cycloalkenyl,
the radicals of group b are optionally being substituted by one or more radicals selected from the group consisting of halogen, cyano, $(C_1-C_4)$alkoxy, $(C_1-C_4)$haloalkoxy;

E is a single bond, or —CH$_2$—;

G is:

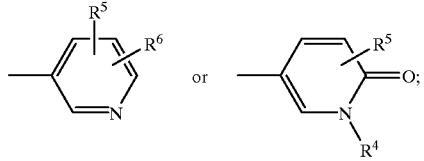

Z is sulfur;

$R^1$, $R^2$ and $R^3$ are H, halogen, $(C_1-C_4)$haloalkyl, $(C_1-C_4)$alkyl, $(C_1-C_4)$alkoxy, $(C_1-C_4)$haloalkoxy or cyano;

$R^4$ is H or $(C_1-C_8)$alkyl which is optionally substituted by one or more radicals selected from the group consisting of halogen, $(C_1-C_4)$alkyl, $(C_1-C_3)$haloalkyl, $(C_1-C_4)$alkoxy, $(C_1-C_3)$haloalkoxy, $(C_1-C_3)$alkylthio, $(C_3-C_8)$cycloalkyl, cyano and tri$(C_1-C_4)$alkylsilyl;

$R^5$ and $R^6$ are
  a) H, halogen, cyano;
  b) $(C_1-C_8)$alkyl, $(C_3-C_8)$cycloalkyl, $(C_4-C_8)$cycloalkenyl, $(C_1-C_8)$alkylthio, $(C_1-C_8)$alkylsulfinyl, $(C_1-C_8)$alkylsulfonyl, $(C_7-C_{12})$phenylalkyl, $(C_7-C_{12})$phenylalkoxy, $(C_4-C_7)$oxycycloalkyl or $(C_4-C_7)$oxacycloalkenyl, each of the above-mentioned groups are optionally substituted by one or more radicals selected from the group consisting of halogen, $(C_1-C_4)$alkyl, $(C_1-C_3)$haloalkyl, $(C_1-C_3)$alkoxy, $(C_1-C_3)$haloalkoxy, $(C_1-C_3)$alkylthio, and cyano; or
  c) $(C_1-C_8)$alkoxy, which is optionally substituted by one or more radicals selected from the group consisting of halogen, $(C_1-C_3)$alkylthio and cyano.

3. The compound as claimed in claim 1 where:

A is phenyl;

X is halogen, $(C_1-C_4)$alkyl, $(C_1-C_3)$haloalkyl, $(C_1-C_4)$alkoxy or $(C_1-C_3)$haloalkoxy;

E is a single bond;

G is 3-pyridyl;

Z is sulfur;

$R^1$, $R^{2,}$ $R^3$ are H$_1$, halogen, $(C_1-C_4)$ haloalkyl, $(C_1-C_4)$ alkyl, $(C_1-C_4)$alkoxy, $(C_1-C_4)$haloalkoxy;

$R^4$ is H or $(C_1-C_8)$alkyl which is optionally substituted by one or more radicals selected from the group consisting of halogen, $(C_1-C_4)$alkyl, $(C_1-C_3)$haloalkyl, $(C_1-C_4)$alkoxy, $(C_1-C_3)$haloalkoxy, $(C_1-C_3)$alkylthio, $(C_3-C_8)$ cycloalkyl, cyano and tri$(C_1-C_4)$alkylsilyl;

$R^5$, $R^6$ are
  a) H, halogen, cyano,
  b) $(C_1-C_8)$alkyl, $(C_1-C_8)$alkoxy, $(C_3-C_8)$cycloalkyl, $(C_4-C_8)$cycloalkenyl, $(C_1-C_8)$alkylthio, $(C_1-C_8)$alkylsulfinyl, $(C_1-C_8)$alkylsulfonyl, $(C_7-C_{12})$phenylalkyl or $(C_7-C_{12})$phenylalkoxy, each of the above-mentioned groups are optionally substituted by one or more radicals selected from the group consisting of halogen, $(C_1-C_4)$alkyl, $(C_1-C_3)$haloalkyl and cyano.

4. A compound as claimed in claim 1 which is:

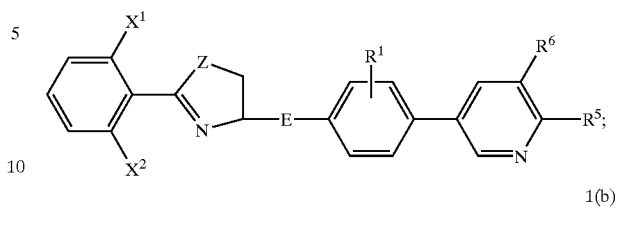

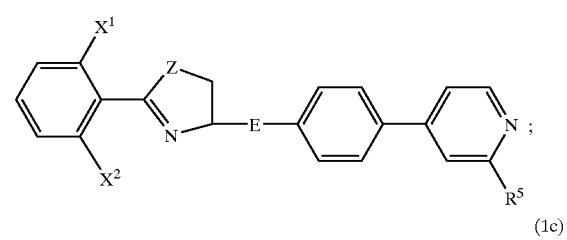

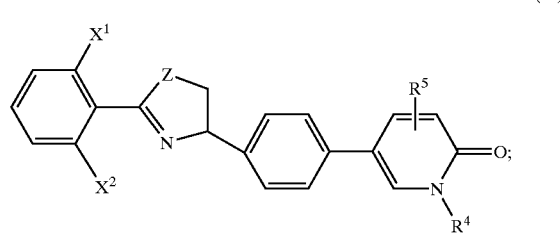

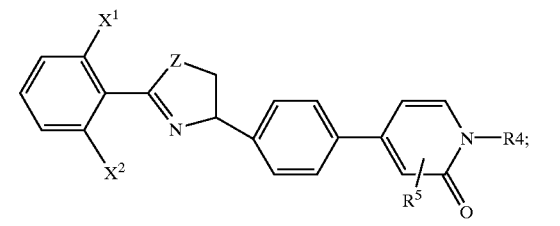

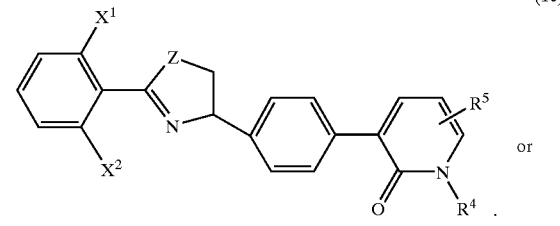

5. The compound in claim 4 which is:

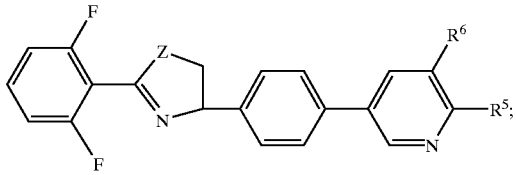

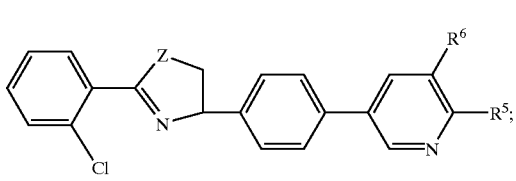

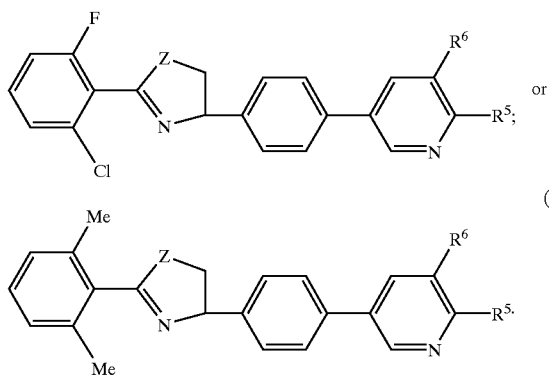

(1a3)

(1a4)

6. The compound according to claim 1, which is:

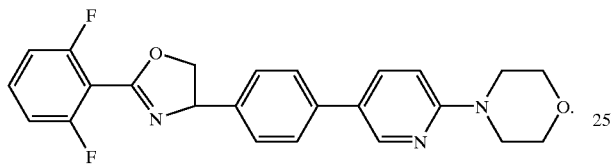

7. A crop protection composition which comprises at least one compound as claimed in claim 1 and at least one formulation auxiliary.

8. A fungicidal composition which comprises a fungicidally effective amount of at least one compound as claimed in claim 1 together with the additives or auxiliaries conventionally used for this application.

9. An insecticidal, acaricidal or nematicidal composition which comprises an effective amount of at least one compound as claimed in claim 1 together with the additives or auxiliaries conventionally used for this application.

10. A veterinary composition which comprises a compound as claimed in claim 1 and at least one formulation auxiliary.

11. A process for the preparation of a composition as claimed in claim 1, which comprises combining the active substance and the other additives and bringing the mixture into a suitable use form.

12. A method of controlling phytopathogenic fungi, which comprises applying a fungicidally effective amount of a compound as claimed in claim 1 to these fungi or to the plants, areas or substrates infested with them, or to seed.

13. A method of controlling harmful insects, Acarina, mollusks and nematodes, in which an effective amount of a compound as claimed in claim 1 is applied to these or to the plants, areas or substrates infested with them.

14. A process for preparing a compound of the formula:

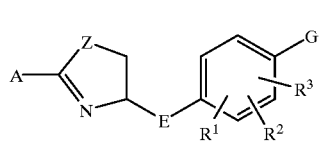

(I)

in claim 1 which comprises reacting a halogen and perfluoroalkylsulfonate compound of the formula:

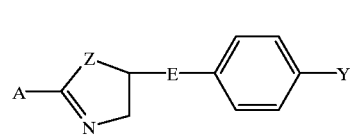

(II)

in which
Y is Cl, Br, I or perfluoroalkylsulfonate and A, Z and E have the meanings given in the formula (I)
with an organometallic compound of the formula (III)

G-M in which
M is a B—, Sn— or Zn— containing leaving group and
G has the meanings given in the formula (I) in claim 1
with palladium catalysis.

* * * * *